United States Patent [19]
Sodroski et al.

[11] Patent Number: 5,852,186
[45] Date of Patent: Dec. 22, 1998

[54] REACTIVE NEUTRALIZING HUMAN ANTI-GP120 RECOMBINANT ANTIBODY, DNA CODING THE SAME AND USE THEREOF

[75] Inventors: Joseph G. Sodroski, Medford; Wayne A. Marasco, Wellesley; Marshall R. Posner, Dedham; William A. Haseltine, Cambridge, all of Mass.

[73] Assignees: Dana-Farber Cancer Insitute, Boston; New England Deaconess Hospital Corp., Dedham, both of Mass.

[21] Appl. No.: 480,774

[22] Filed: Jun. 7, 1995

Related U.S. Application Data

[62] Division of Ser. No. 400,674, Mar. 8, 1995, abandoned, which is a continuation of Ser. No. 804,652, Dec. 10, 1991, abandoned.

[51] Int. Cl.$^6$ .......................... C07H 21/04; A61K 39/42; C07K 16/10
[52] U.S. Cl. .................................... 536/23.53; 424/133.1; 424/135.1; 424/148.1; 435/69.6; 435/70.21; 435/172.2; 435/172.3; 435/328; 435/339.1; 435/252.3; 435/252.33; 530/387.3; 530/388.35
[58] Field of Search ............................. 424/133.1, 135.1, 424/142.1, 148.1, 160.1; 435/69.6, 69.7, 70.21, 172.2, 172.3, 328, 339.1, 252.3, 252.33, 320.1; 530/387.3, 388.15, 388.35, 389.4; 536/23.53

[56] References Cited

U.S. PATENT DOCUMENTS 5,215,913 6/1993 Posner ................................ 530/388.15

FOREIGN PATENT DOCUMENTS

WO91/13148 9/1991 WIPO .

OTHER PUBLICATIONS

Barre–Sinoussi, et al., Science, 220:868–871 (1983).
Gallo, et al., Science 224:500–503 (1984).
Levy, et al., Science, 225:840–842 (1984).
Popovic, et al., Science, 224:497–500 (1984).
Sarngadharan, et al., Science 224:506–508 (1984).
Siegal, et al., New England Journal of Medicine, 305:1439–1444 (1981).
Zagury, et al., Science 231:850–853 (1986).
Patner, et al., Nature, 313:277–284 (1985).
Sanchez–Pescador, et al., Science, 227:484–492 (1985).
Muesing, et al., Nature, 313:450–457 (1985).
Wain–Hobson, et al., Cell, 40:9–17 (1985).
Sodroski, et al., Science, 231:1549–1553 (1986).
Arya et al., Science, 229:69–73 (1985).
Sodroski, et al., Nature, 321:412–417 (1986).
Feinberg, et al., Cell, 46:807–817 (1986).
Haseltine, Journal of Acquired Immune Deficiency Syndrome, 1:217–240 (1988).
Cohen, et al., Nature, 334:532–534 (1988).
Wang–Staal, et al., AIDS Res. and Human Retro Viruses, 3:33–39 (1987).
Guyader, et al., Nature, 326:662–669 (1987).
Chakrabarti, et al., Nature, 328:543–547 (1987).
Berger, et al., PNAS, 85:2357–2361 (1988).
Dalgleish, et al., Nature, 312:763–767 (1984).
Kaltzmann, et al., Nature, 312:767–768 (1984).
Fauci, et al., Ann. Int. Med., 100:92–99 (1984).
Haigwood, et al., Vaccines, 90:313–320 (1990).
Steimer, et al., Science, 254:105–108 (1991).
Rusche, et al., PNAS, 85:3198–3202 (1988).
Goudsmit, et al., PNAS, 85:4478–4482 (1988).
Palker, et al., PNAS, 85:1932–1936 (1988).
Kang, et al., PNAS, 88:6171–6175 (1991).
McKeating, et al., AIDS, 3:777–783 (1989).
Looney, et al., Science, 241:357–360 (1988).
Ho, et al., J. Virol. 61:2024–2028 (1987).
Nara, et al., J. Virol., 61:3173–3180 (1988).
Goudsmit, et al., Vaccine, 6:229–238 (1988).
McDougal, et al., J. Immunol., 137:2937–2944 (1986).
Ardman, et al., J. AIDS, 3:206–214 (1990).
Schnittman, et al., J. Immunol. 141:4181–4186 (1988).
Olshevsky, et al., J. Virol., 64:5701–5707 (1990).
Thali, et al., J. Virol., 65:6188–6193 (1991).
Posnēr, et al., J. Immunol., 146:4325–4332 (1991).
Marks, et al., J. Mol. Biol., 222:581–597 (1991).
McCafferty, et al., Nature, 348:552–554 (1990).
Winter, et al., Nature, 349:293–299 (1991).
Fahey, et al., Clin. Exp. Immunol., 88:1–5 (1992).
Morrison, et al., Proc. Natl. Acad. Sci. USA, 81:6851–6855 (1984).
Queen, et al., Proc. Natl. Acad. Sci. USA, 86:10029–10033 (1989).
Huston, et al., Proc. Natl. Acad. Sci. USA, 85:5879–5883 (1988).

*Primary Examiner*—Robert D. Budens
*Attorney, Agent, or Firm*—David G. Conlin; David S. Resnick; Ronald I. Eisenstein

[57] ABSTRACT

The present invention is directed to a recombinant human monoclonal antibody which binds to a discontinuous epitope on the HIV gp120 envelope glycoprotien, blocks the binding of gp120 to the CD4 receptor, and neutralizes a broad range of HIV isolates. The present invention also provides the primary nucleotide and deduced amino acid sequences of the rearranged heavy and light chains of the recombinant monoclonal antibody of the present invention, and a method of screening for antibodies which block binding of envelope glycoprotein to the CD4 receptor.

6 Claims, 16 Drawing Sheets

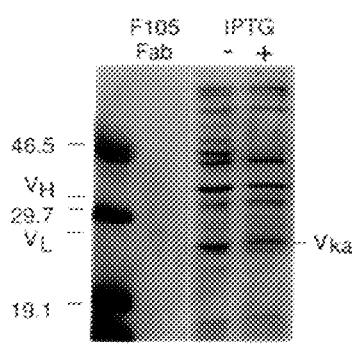 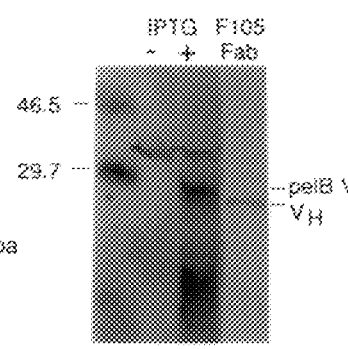 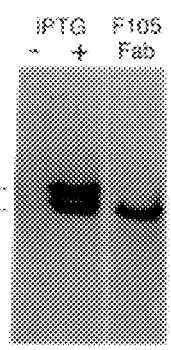
F I G. 4A          F I G. 4B          F I G. 4C

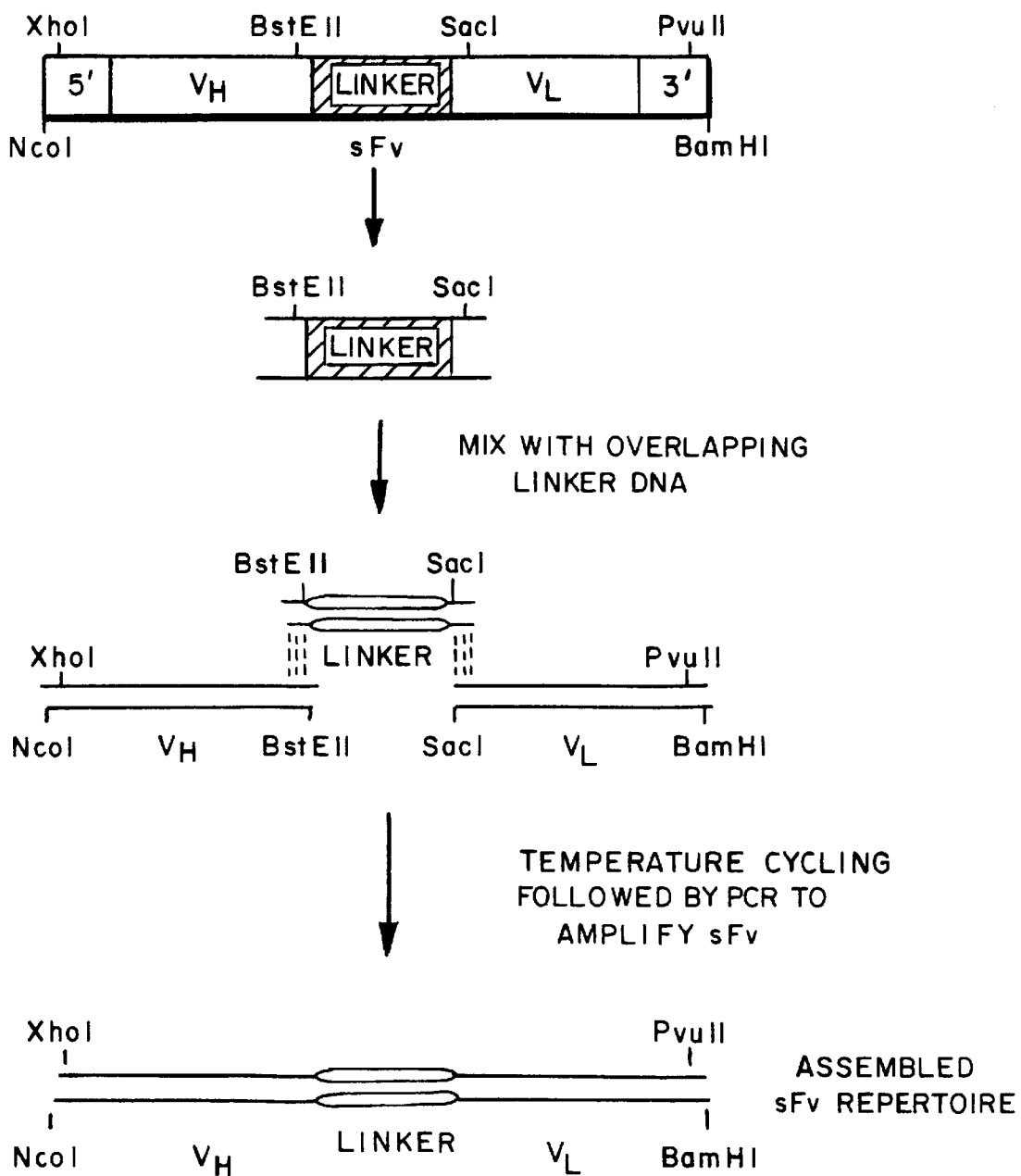
FIG. II

 
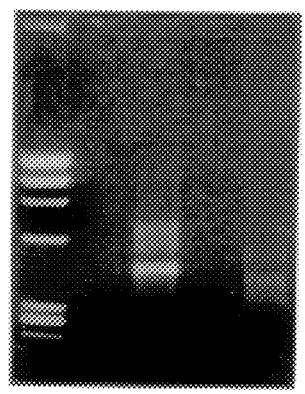 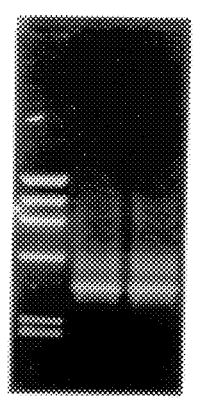
FIG. 14　　　　FIG. 15

REACTIVE NEUTRALIZING HUMAN ANTI-GP120 RECOMBINANT ANTIBODY, DNA CODING THE SAME AND USE THEREOF

This application is a divisional application of application Ser. No. 08/400,674, filed Mar. 8, 1995, now abandoned, which is a continuation of application Ser. No. 07/804,652, filed Dec. 10, 1991, now abandoned.

FIELD OF THE INVENTION

The present invention is directed to a recombinant human monoclonal antibody which binds to a discontinuous epitope on the HIV gp120 envelope glycoprotein, blocks the binding of gp120 to the CD4 receptor, and neutralizes a broad range of HIV isolates. The present invention also provides the primary nucleotide and deduced amino acid sequences of the rearranged heavy and light chains of the recombinant monoclonal antibody of the present invention, and a method of screening for antibodies which block binding of envelope glycoprotein to the CD4 receptor.

BACKGROUND OF THE INVENTION

The human immunodeficiency virus (HIV-1, also referred to as HTLV-III, LAV or HTLV-III/LAV) is the etiological agent of the acquired immune deficiency syndrome (AIDS) and related disorders. [Barre-Sinoussi, et al., *Science*, 220:868–871 (1983); Gallo, et al., *Science*, 224:500–503 (1984); Levy, et al., *Science*, 225:840–842 (1984); Popovic, et al., *Science*, 224:497–500 (1984); Sarngadharan, et al., *Science*, 224:506–508 (1984); Siegal, et al., *New England Journal of Medicine*, 305:1439–1444 (1981)]. This disease is characterized by a long asymptomatic period followed by the progressive degeneration of the immune system and the central nervous system. Studies of the virus indicate that replication is highly regulated, and both latent and lytic infection of the CD4 positive helper subset of T-lymphocytes occur in tissue culture [Zagury, et al., *Science*, 231:850–853 (1986)]. The expression of the virus in infected patients also appears to be regulated as the titer of infectious virus remains low throughout the course of the disease. Molecular studies of the replication and genomic organization of HIV-1 show that it encodes a number of genes [Ratner, et al., *Nature*, 313:277–284 (1985); Sanchez-Pescador, et al., *Science*, 227:484–492 (1985); Muesing, et al., *Nature*, 313:450–457 (1985); Wain-Hobson, et al., *Cell*, 40:9–17 (1985)]. Three of the genes, the gag, pol and env genes are common to all retroviruses. The genome also encodes additional genes that are not common to most retroviruses, the tat, rev (formerly referred to as art), nef, vif, vpr and vpu genes [Sodroski, et al., *Science*, 231:1549–1553 (1986); Arya, et al.,. *Science*, 229:69–73 (1985); Sodroski, et al., *Nature*, 321:412–417 (1986); Feinberg, et al., *Cell*, 46:807–817 (1986); Haseltine, *Journal of Acquired Immune Deficiency Syndrome*, 1:217–240 (1988); Cohen, et al., *Nature*, 334:532–534 (1988); Wong-Staal, et al., *AIDS Res. and Human Retro Viruses*, 3:33–39 (1987) which are all incorporated herein by reference.].

Nucleotide sequences from viral genomes of other retroviruses, particularly HIV-2 and simian immunodeficiency viruses, SIV (previously referred to as STLV-III), also contain the structural genes including env as well as regulatory sequences such as tat, rev and nef [Guyader, et al., *Nature*, 326:662–669 (1987); Chakrabarti, et al., *Nature*, 328:543–547 (1987), which are incorporated herein by reference]. These three HIV viruses share a similar genetic organization, even though there can be sequence variations.

The env genes of HIV-1, HIV-2 and SIV all produce an envelope glycoprotein, which is cleaved, with one portion being an exterior viral envelope protein subunit referred to as gp120. The binding and fusion of HIV-1, HIV-2 and SIV viruses with cells is mediated by specific interaction between the external subunit of this gp120 viral envelope protein and the CD4 receptor on the target cell surface [Berger, et al., *PNAS*, 85:2357–2361 (1988)].

The first step in infection by HIV is the specific binding of gp120, the envelope glycoprotein, to its cellular receptor, the CD4 molecule [Dalgleish, et al., *Nature*, 312:763–767 (1984); Klatzmann, et al., *Nature*, 312:767–768 (1984)]. Infection with HIV leads, in most cases, to a progressive decline in the number and functions of CD4+ T cells with the eventual appearance of clinical manifestations of cellular immunodeficiency, such as opportunistic infections and malignancies, i.e., AIDS [Fauci, et al., *Ann. Int. Med.*, 100:92–99 (1984)].

Serum antibodies reacting with the HIV-1 gp120 can neutralize viral infection by binding to several sites on the molecule [Haigwood, et al., *Vaccines*, 90:313–320 (1990); Steimer, et al., *Science*, 254:105–108 (1991)]. The earliest neutralizing human antibody response is directed to epitopes in the third hypervariable region of gp120, the principle neutralizing domain, which is contained within a loop formed by disulfide bonding [Rusche, et al., *PNAS*, 85:3198–3202 (1988); Goudsmit, et al., *PNAS* 85:4478–4482 (1988); Palker, et al., *PNAS*, 85:1932–1936 (1988)]. These antibodies are frequently strain-specific [Kang, et al., *PNAS*, 88:6171–6175 (1991)]. Envelope glycoprotein variation both within the linear epitope and outside the epitope can allow escape of viruses from neutralization by these antibodies [McKeating, et al., *AIDS*, 3:777–783 (1989); Looney, et al., *Science*, 241:357–360 (1988)]. Later in the course of HIV infection, more broadly neutralizing antibodies appear [Ho, et al., *J. Viro.*, 61:2024–2028 (1987)]. A large fraction of these broadly neutralizing antibodies, which are present in low concentrations in patients' sera, are directed to conformationally sensitive epitopes on gp120 [Nara, et al., *J. Viral.*, 61:3173–3180 (1987); Goudsmit, et al., *Vaccine*, 6:229–238 (1988)]. A subset of the broadly reactive antibodies, found in the serum of patients, interferes with the binding of gp120 and CD4 [Steimer, et al., supra; Rusche, et al., supra; McDougal, et al., *J. Immunol.*, 137:2937–2944 (1986); Ardman, et al., *J. AIDS*, 3:206–214 (1990); Schnittman, et al., *J. Immunol.*, 141:4181–4186 (1988)]. These antibodies appear to be reactive with a discontinuous epitope on gp120 which encompasses the CD4 binding region [Olshevsky, et al., *J. Virol.*, 64:5701–5707 (1990);. Thali, et al., *J. Virol.*, 65:6188–6193 (1991)]. This region of gp120 is well-conserved, although not invariant.

One such antibody, a monoclonal antibody (Mab), referred to as is F105, an IgG1K Mab, neutralizes a number of diverse HIV-1 isolates and reacts with a conformationally defined epitope on HIV-1/gp120 that appears to be within, or topographically near, the CD4-binding site. In addition, F105 has been reported to block the binding of $HIV_{III\,B}$ to HT-H9 cells and prevents infection of these cells at suitable concentration. [Thali, et al., supra; Posner, et al., *J. Immunol.*, 88:6171–6175 (1991)]. However, this antibody has only been isolated from hybridomas. Thus, it is available in only small amounts and at low purity. It would be useful if such an antibody were produced by recombinant DNA techniques. This would permit the availability of a recombinant DNA encoding the antibody would allow for the production of mutant forms of the antibody having greater antigen affinity. Furthermore, it would be desirable to be able to increase the binding affinity of this antibody and to be able to tailor this antibody to enhance and increase the HIV and SIV strains that the antibody will neutralize. It would also be desirable to know the nucleotide sequence of the DNA encoding this antibody. Understanding the molecular nature of the broadly neutralizing human antibodies which are directed at or near the CD4 binding domain of gp120 is important for diagnosis and treatment of immunodeficiency diseases.

SUMMARY OF THE INVENTION

In accordance with the present invention, Applicants have now produced a recombinant monoclonal antibody having binding activity at or near the CD4 binding domain of gp120. The primary nucleotide and deduced amino acid sequences of the rearranged heavy and light chains of the recombinant monoclonal antibody of the present invention are also disclosed. The recombinant antibody of the present invention neutralizes a wide range of diverse HIV and SIV isolates, preferably HIV-1 isolates. It preferably reacts with a conformationally defined epitope on HIV-1/gp120 which, while not wishing to be bound by theory, appears to be topographically near the CD4-binding site.

A method for treating or minimizing immunodeficiency diseases in mammals, particularly in humans, is also disclosed. This method comprises administering a therapeutic amount of the antibody of the present invention to prevent and/or obstruct HIV infection. Another aspect of the present invention relates to conjugates of the recombinant monoclonal antibody of the present invention, and a cytotoxic moiety, for example an immunotoxin.

In another embodiment, this invention permits a simple assay for diagnosis and study of the progression of disease in patients and volunteers by screening for the DNA.

This invention also permits a simple assay to screen for and clone for other antibodies having varying degrees of binding affinity to gp120 epitopes. Preferably, the gp120 epitope is at or near the CD4-binding site.

BRIEF DESCRIPTION OF THE DRAWINGS

FIGS. 1-1 and 1-2 are schematics that shows the immunoglobulin genes and location of PCR primers. The heavy (FIG. 1A) and light (FIG. 1B) chain immunoglobulin genes are shown with V, D, and J segments noted as well as the constant regions. Also depicted are the CDR regions. The primers for PCR amplification of genomic DNA or cONA are shown, for both Fv and Fab gene amplification.

FIG. 2 is a schematic that shows the strategy for cloning the $V_H$ and $V_L$ genes into the pEtpelB vector.

FIG. 3 is a schematic that shows strategies for $V_H$ and $V_L$ expression from a single vector and the construction of the single chain Fv (sFv) expresser.

FIG. 4A–FIG. 4C show the production of F105 Fab antibody fragment using the pETpelB vector (rF105 Fab). The plasmid pETpelBTag (containing F105 rearranged $V_H$ and $V_L$ genes) was transformed into BL21(DE3) and after reaching O.D.$_{600}$ of 0.6 was induced with 1 mM IPTG (control-no IPTG). Bacteria were harvested after a 2-hour incubation at 37° C. FIG. 4A. Coomassie Blue staining of a 12.5% SDS-polyacrylamide gel of total cell lysates. FIG. 4B. Western blot of F105 $V_H$-tag fusion protein probed with rabbit anti-$V_H$-4FR1 [Silverman, et al., *Eur. J. Immunol.*, 20:351–356 (1990)] (a gift from Dr. Gregg Silverman, University of California, San Diego). High levels of $V_H$ proteins were induced in this plasmid/host system only after induction with IPTG. No specific proteins were detected in Western blots of control BL21(DE3) bacteria containing the pETpelB vector with no $V_H$ gene insert, even after IPTG induction [data not shown]. Rabbit anti-angiotension I (anti-tag) when used as primary antibody gave identical results [data not shown]. FIG. 4C. Western blot of F105 $V_L$ protein probed with goat anti-κ chain antibody (Souther Biotechnology Associates). The upper band represents precursor protein prior to pel B signal cleavage and has been seen in other constructs (Glockshuber, et al., *Biochem.*, 29:1362–1367 (1990)].

FIG. 5 shows the detection of gp120 binding activity with rF105 Fab produced in BL21(DE3). Two hours after induction with 1 mM IPTG, a periplasm subcellular fraction was obtained from BL21(DE3) transformed with pETpelB tag vector containing the F105 Fab cassette. Concentrated samples of periplasm fractions were then incubated on rgp120 coated ELISA plates (American Biotechnology, Inc., Cambridge, Mass.). Binding of both F105 Fab (produced by papain cleavage) and rF105 Fab to gp120 was detected with goat anti-κ chain antibody followed by immuno-detection using alkaline phosphatase as enzyme.

FIG. 6 shows the results of affinity column purification of rF105 Fab antibody fragments. Periplasm preparations of BL21(DE3) transformed with pETpelB tag vector containing the F105 Fab cassette were passed through a gp120 affinity column. Bound rF105 Fab was eluted with glycine-HCl (pH2.6) followed by neutralization with 1M Tris-HCl (pH8.0). The pooled fractions were then analyzed by ELISA on gp120 coated plates as in FIG. 5.

FIG. 7 is a representation showing a method used for the direct generation of random combinatorial libraries expressed as sFvs. The 5' tails of the reverse $J_H$ primer and the forward $V_\kappa$ primer consist of 45 nucleotides perfectly complementary to one another and encoding for the interchain linker sequence (Gly$_4$-Ser)$_3$. An internal interchain linker restriction site BspE I has also been introduced and the $J_H$ and $V_\kappa$ linker boundaries contain BstE II and Sac I sites to facilitate future linker swapping experiments. The heavy and light chains are separately amplified by PCR, digested with BspE I and ligated in frame through BspE I cohesive ends. This permits us not to add an interchain linker and at the same time serves to produce a random combinatorial library of sFvss. The 750-bp product (sFv) will be gel-purified and following digestion with the appropriate enzymes, the sFvs will be cloned directly into the pETpelB expression vector or into the intermediate double stranded fd-tet phage antibody expression.

FIG. 8 is a schematic that shows the production of F105 sFV antibody by single step cloning. Digestion of the heavy and light chain PCR fragments with Not I/BspE I and BspE I/Xba I, respectively, showed by ligation resulted in the successful cloning of F105 sFv in pSL1180. This cassette was then removed by Not I/Bgl II digestion and cloned into the small pETpelB expression vector. Note that for this F105 sFV construct, a PCR primer containing a 5' $V_H$ Not I site was used in place of the Nco I site and the corresponding pETpelB signal sequence containing the Not I cloning site was used.

FIG. 9A–FIG. 9C shows the production of F105 sFv antibody fragment using the pETpelB vector (rF105 sFv). The plasmid pETpelB (containing F105 sFv genes) was transformed into BL21(DE3) and after reaching O.D.$_{600}$ 0.6 was induced with 1 mM IPTG (control-no IPTG). Bacteria were harvested after a 2-hour incubation at 37° C. FIG. 9A.

Coomassie Blue staining of a 12.5% SOS-polyacrylamide gel of total cell lysates. FIG. 9B. Western blot of F105 sFv protein probed with rabbit anti-$V_H$FR1 antisera. FIG. 9C. Western blot of F105 sFv protein probed with goat anti-κ chain antibody.

FIG. 10 shows the results of affinity column purification of rF105 sFV antibody fragments. Periplasm preparation of BL21(DE3) transformed with pETpelB vector containing the F105 sFv cassette was passed through a gp120 affinity column. Bound rF105 sFv was eluted with glycine-HCl (pH 2.6) followed by neutralization with 1M Tris-HCl (pH 8.0). The pooled fractions were then analyzed by ELISA on gp120 coated plates.

FIG. 11 is a schematic that shows the design for F105 derived interchain linker primer for the amplification of hierarchical and random combinatorial libraries. In this embodiment, F105 sFv is used for the PCR amplification of the $(Gly_4-Ser)_3$ interchain linker which contains a flanking 5' $J_H$ framework sequence and a 3'$V_\kappa$ framework sequence.

Figures 1, 13:
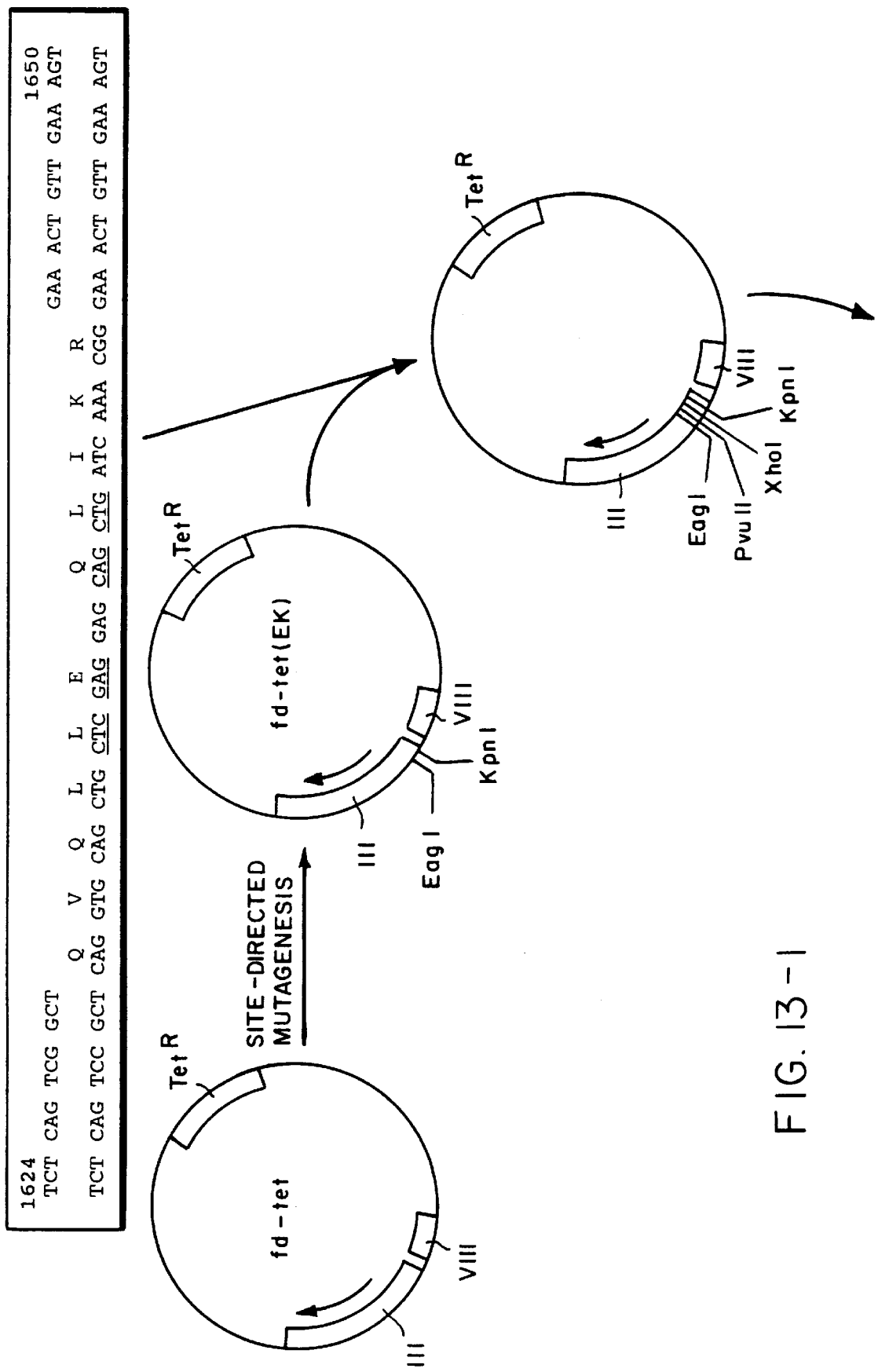
Figures 2, 13:
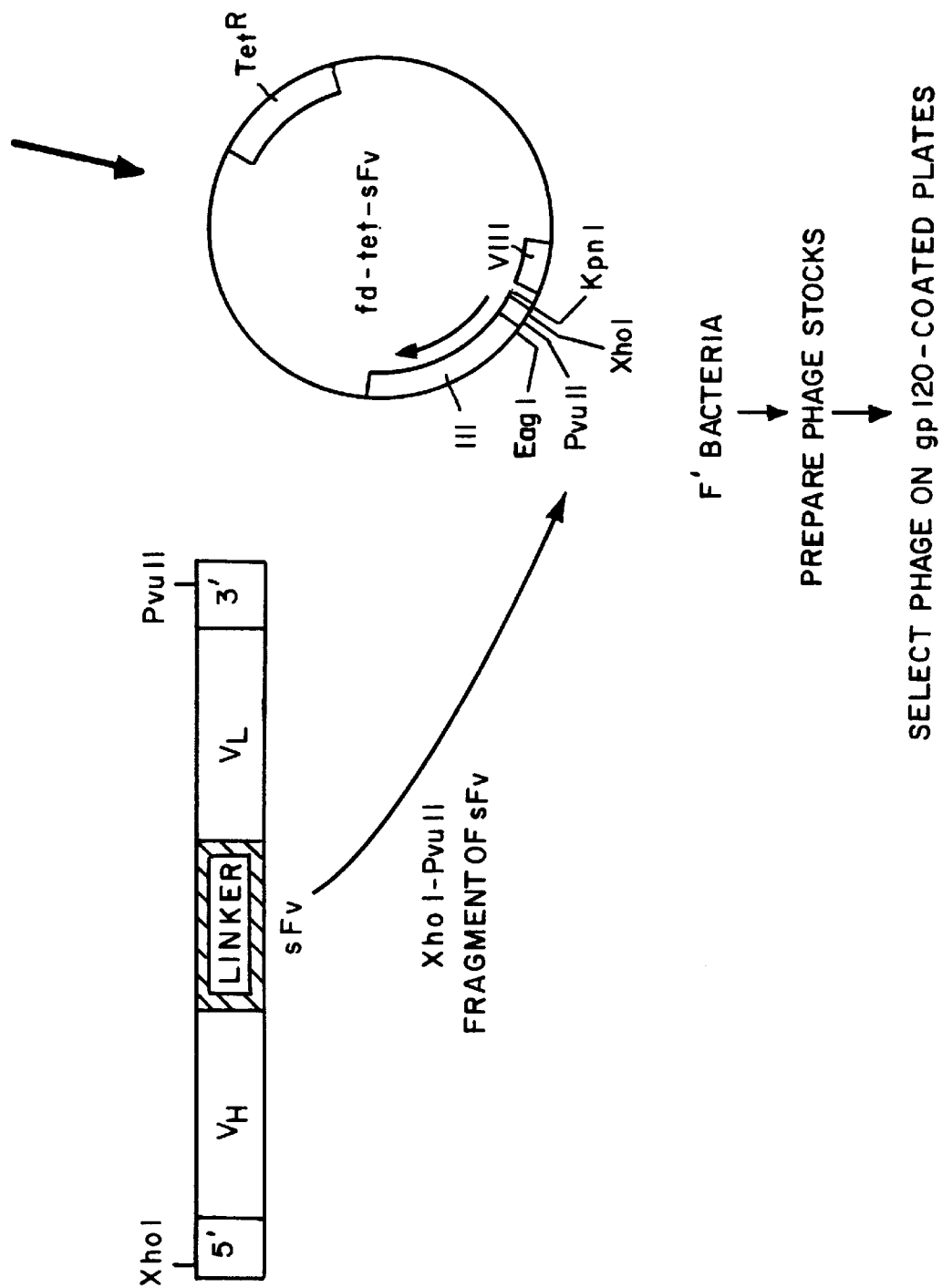

FIG. 13 is a schematic representation showing the generation of phage antibodies. The fd-tet plasmid, encoding replication-competent fd phage, will be used to generate single-stranded DNA for mutagenesis. Kpn I and Eag I sites will be introduced into gene III, which encodes the absorption protein for attachment to the bacterial F pilus, without changing the amino acid coding sequence of gene III. A synthetic oligonucleotide, which introduces the junctions of the single chain sFV gene in-frame with gene III, will be inserted into the Kpn I and Eag I sites. The remainder of the sFv insert will then be cloned into the sFv using Xho I and Pvu II sites.

FIGS. 14 and 15 shows the PCR amplification of hierarchical and random combinatorial immunoglobulin genes from the PBL's of HIV-1-infected patient HIV-51. The hierarchical library is produced by PCR amplification using $V_H$ 71-4 and Humvk325 leader sequence primers, whereas for the heavy chain genes, the random combinatorial library is produced by PCR amplification using the degenerate $V_H$ primer. Thirty PCR cycles were used in this experiment with 5% of the cDNA.

DETAILED DESCRIPTION OF THE INVENTION

The present invention is directed to a monoclonal antibody produced by recombinant technology. For example, the gene encoding, the rearranged gene for heavy chain or light chain variable domain may be produced, for instance, by cloning or gene synthesis, and placing them into a suitable expression vector. The expression vector is then used to transform a compatible host cell which is then cultured to allow the immunoglobulin or fragment thereof to be expressed and, preferably secreted. The skilled artisan can use a single chain cloning strategy or a dual chain strategy. The single chain method is preferred.

In accordance with the present invention, cDNA encoding the F105 rearranged variable region heavy chain and variable region light chain has been cloned and their nucleotide sequences, and deduced amino acid sequences are set out in the sequence listing as SEQ ID NO:1, SEQ ID NO:2, SEQ ID NO:3, and SEQ ID NO:4.

One method that can be used to clone the F105 heavy and light variable regions ($V_H$ and $V_L$, respectively) is to synthesize or screen for SEQ ID NO:1 and SEQ ID NO:3.

Thereafter, prepare a DNA segment containing SEQ ID NO:1 or SEQ ID NO:3 operably linked to a promoter which will express the sequence in a procaryotic and/or eukaryotic host of choice. Such promoters can readily be chosen by the skilled artisan depending upon the particular host cell the skilled artisan wishes to use as a host. For example, viral promoters, such as φ10 or SV40 are preferred. Preferably, the DNA segment contains both SEQ ID NO:1 and SEQ ID NO:3. One can use a flexible linker peptide such as SEQ ID NO:5 (Gly-Gly-Gly-Gly-Ser)$_3$. SEQ ID NO:1 and SEQ ID NO:3 can be operably linked to the same promoter or operably linked to other promoters.

One method for preparing such DNA segments combines the following elements [Huse, et al., *Science*, 246:1275–1281 (1989)]:

1. isolating nucleic acids containing a substantial portion of the immunological repertoire;
2. preparing polynucleotide primers for cloning polynucleotide segments containing immunoglobulin $V_H$ and/or $V_L$ region genes;
3. preparing a gene library containing a plurality of different $V_H$ and $V_L$ genes from the repertoire.

Thereafter, one can express the $V_H$ and/or $V_L$ polynucleotides in a suitable host, including procaryotic and eukaryotic hosts, either separately or in the same cell, and either on the same or different expression vectors; and screen the expressed polypeptide for a preselected activity (e.g., affinity binding to gp120, in vitro neutralizing ability for HIV (and/or SIV) isolates) and segregate the $V_H$- and/or $V_L$-coding gene identified by the screening process. Such affinity and neutralizing assay are set forth in detail below.

Nucleic acid containing a substantial portion of the immunological gene repertoire may be isolated from a heterogeneous population of antibody-producing cells, i.e., B-lymphocytes (B cells), preferably rearranged B cells such as those found in the circulation or spleen of a vertebrate which has been infected with HIV, HIV vaccines or, immunized or partially immunized with HIV or the gp120 envelope glycoprotein. Such lymphocytes include, for example, peripheral blood lymphocytes (PBLs).

Preferably, in accordance with the present invention, the DNA sequence encoding the immunoglobulin is isolated from a hybridoma which secretes the monoclonal antibody. Such a hybridoma can be easily producing using methods available in the art [Kohler, et al., *Nature*, 256:495 (1975) which is incorporated by reference]. Typically, this involves fusing an antibody producing cell with an immortal cell line such as a myeloma cell to produce the hybrid cell.

In one example, hybridomas can be generated by immunization of mice with the gp120 envelope glycoprotein. The mice can be immunized intraperitioneally (i.p.) with a sufficient amount of peptide. This can then be followed immediately by an i.p. injection of, for example, cyclophosphamide in $H_2O$. The cyclophosphamide treatment is repeated one and two days following the primary injection. About two weeks following immunization, mice are again injected with a sufficient amount of the peptide and then allowed to rest for another two weeks. Four days following the second injection, the animals are sacrificed and their spleens obtained for the first fusion.

Hybridomas are produced by fusing cells by typical techniques, such as from immunized mice with SP2/0 myeloma cells by a polyethylene glycol (PEG) method. Cells are aseptically removed from immunized mice and a single cell suspension of the spleen cells obtained by per-fusing the spleen with serum-free media (e.g., DME). Spleen cells and myelomas cells are mixed together at a ratio, for example, 5 to 1, spleen cells to myelomas cells. The cells are then centrifuged and the supernatant removed by aspiration. The cells are then grown in medium by standard techniques. Hybridomas, which grow after the fusion procedure, are then screened for secretion of antibodies specific to the gp120 epitopes by an ELISA assay on a cells lysate. Hybridomas, that produce positive results, are expanded and cloned by limiting dilution to assure that the cells and resulting antibodies are indeed, monoclonal. Hybridoma colonies that test positive for the presence of antibody to one of the desired gp120 epitopes are diluted in media to a concentration of, for example, 5 hybridoma cells per milliliter. Once colonies grow, the supernatants are again tested for the presence of antibody to the gp120 epitope. If the results are positive when tested by an ELISA assay, the colonies are cloned again by limiting dilution.

In one preferred embodiment, one uses an HIV-1 or HIV-2 gp120 to elicit production of antibodies. The use of HIV-1 gp120 is presently preferred.

In a preferred embodiment, the DNA is obtained from the F105 hybridoma derived by fusion of EBV transformants with the HMMA2.11TG/0 cell line, a non-secreting human-mouse melanoma analog [Posner, et al., *J. Immunol.*, 88:6171–6175 (1991)].

The immunoglobulin genes of the present invention can be isolated from either genomic material containing the gene expressing the variable region or the messenger RNA (mRNA) which represents a transcript of the variable region. When using genomic DNA from other than non-rearranged B-lymphocytes care should be taken in positioning the sequences coding for the variable region because the sequences are separated by introns. This can readily be done by the skilled artisan based upon the present disclosure. The DNA fragment(s) containing the proper exons are isolated, the introns excised and the introns then spliced in proper order and in proper orientation. An alternative technique employing rearranged B cells is preferred because the CD and J immunoglobulin gene regions have translocated to become adjacent, so that the sequence is continuous (free of introns) for the the entire variable region. Where mRNA is utilized the cells must be lysed under RNAse inhibiting conditions. mRNA may be separated from other RNA by oligo-dT chromatography. A complementary strand of cDNA may then be synthesized on the mRNA template, using reverse transcriptase and a suitable primer, to yield an RNA-DNA heteroduplex [Gubler, et al., *Gene*, 25:263–269 (1983)]. A second strand of DNA can be made one of several ways, for example, by priming with RNA fragments of the mRNA strand (made by incubating RNA-DNA heteroduplex with RNAse H), and using DNA polymerase, or by priming with a synthetic oligodeoxynucleotide primer which anneals to the 3' end of the first strand and using DNA polymerase.

When making such ds cDNA, it is possible to use a forward primer which anneals to a sequence in the CH1 domain (for a heavy chain variable domain) or the Cλ or CX domain (for a light chain variable domain). These primers are located in a proximity that is close enough to the target sequence to allow the sequence to be cloned, and can readily be determined from the present disclosure.

The back primer may be one which anneals to a sequence at the N-terminal end of VH1, VX or Vλ domain. The back primer may consist of plurality of primers having a variety of sequences designed to be complementary to the various families of VH1, VX or Vλ sequences known. Alternatively, the back primer may be a single primer having a consensus sequence derived from all the families of variable region genes.

The oligonucleotide primers may be specifically designed for use with a particular target sequence, for example based upon such sequences from SEQ ID NO:1 and/or SEQ ID NO:3.

To amplify the $V_H$-coding and $V_L$-coding DNA homologs using polymerase chain reaction amplification, two primers must be used for each coding strand of nucleic acid to be amplified. The first primer becomes part of the non-sense, (minus or complementary) strand and hybridizes to a nucleotide sequence conserved among $V_H$ (plus) strands within the repertoire. To produce $V_H$ coding DNA homologs, first primers are therefore chosen to hybridize to (i.e., complementary to) conserved regions within the J region, CH1 region, hinge region, CH2 region or CH3 region of the immunoglobulin genes. Primers to the J, CH1 and hinge regions are preferred. To produce a $V_L$ coding DNA homolog, first primers are chosen to hybridize with a conserved region within the J region or a constant region of immunoglobulin light chain genes. To produce the $V_H$-coding DNA homologs, second primers are chosen to hybridize with a conserved nucleotide sequence at the 5' end of the $V_H$-coding immunoglobulin gene, such as in that area coding for the leader or first framework region. In amplification of both $V_H$- and $V_L$-coding DNA homologs, the conserved 5' nucleotide sequence of the second primer can be complementary to the sequence exogenously added using terminal deoxynucleotidyl transferase as described by Loh, et al., *Science*, 243:217–220 (1989). One or both of the first and second primers can contain a nucleotide sequence defining an endonuclease restriction site. The site can be heterologous to the immunoglobulin gene being amplified, and typically appear at or near the 5' end of the primer. The use of primers with restriction sites has the advantage that the DNA can be cut with at least one restriction enzyme which leaves 5' or 3' overhanging nucleotides. Such DNAs are more readily cloned into the corresponding sites on the vector than blunt-ended fragments taken directly from the method. The double-stranded cDNA produced at the end of the cycles is readily insertable into a cloning vector by using an appropriate restriction enzyme, which can be chosen empirically based upon the present disclosure. Preferably, the choice of restriction sites is such that the ds cDNA is cloned directly into an expression vector, such that the immunoglobulin or fragment thereof encoded by the gene is expressed.

Preferably, the heavy chain primer pair consists of a $V_H$ primer and a $J_H$ primer, each containing convenient restriction sites for cloning. Using for example, the Kabat database on immunoglobulins [Kabat, et al., "Sequences of Proteins of Immunological Interest", 4th Ed. (U.S. Department of Health and Human Services) (1987)], one can analyze the amino acid and codon distribution found in the six distinct human $V_H$ families. For example, the 35 base pair 5' $V_H$ primer was designed to be degenerate for two different nucleotides at four positions. A Not I site, can be used for cloning the amplified DNA, and is located immediately 5' to the first codon of the $V_H$ gene. See FIG. 1A. Similarly, a 35 base pair $J_H$ region oligonucleotide can be designed for reverse priming at the 3' end of the heavy chain variable gene. Based on the nucleotide sequence of the six human $J_H$ region minigenes, this primer contains three degenerate positions with two nucleotides at each position. A BssH II site 3' to and immediately adjacent to the codon determining the last amino acid of the J region allows for convenient cloning at the 3' end of the $V_H$ gene.

A similar strategy can be used to design PCR primers for the human light chain variable genes. See, FIG. 1B. Primers for amplification of human κ ($V_κ/J_κ$ pair) or λ ($V_λ/J_λ$ pair) light chain genes are synthesized using, for example, the Kabat database as a guide. With regards to the κ light chain region primers, since there are four families of human $V_κ$ genes, the 5' $V_κ$ primer is preferably degenerate at three positions (two nucleotides each) and contains a Not I site at a position similar to that of the $V_H$ region primer described above. The reverse 39 base pair Jκ primer, designed from the sequence of five human $J_κ$ minigenes, is preferably degenerate at three positions (two nucleotides at each position) and contains a BamH I site flanking the $J_κ$ coding region. Identical restriction endonuclease sites are present on the primers for the λ light chain genes.

The primers do not need to have a sequence exactly complementary to the target sequence to which it is annealed, differences can arise for instance because of nucleotide variations or because of the introduction of a restriction enzyme site. One can adjust conditions in the annealing mixture to enable the primers to anneal to the ds nucleic acid by making annealing conditions less stringent. This is well within the competence of the person skilled in the art.

The DNA polymerase used in this method may be any DNA polymerase known in the art, for example any of those commercially available. The conditions to be used for each polymerase are well known. The polymerase reaction will be carried out in the presence of the four nucleoside triphosphates. These and the polymerase enzyme may already be present in the sample or may be provided afresh for each cycle.

Denaturing of the DNA strands may be carried out by any known method, for instance, by heating the sample. When heating is used to control the method, a suitable cycle of heating comprises denaturing at about 95° C. for about one minute, annealing at from 30° C. to 65° C. for about one minute, and primer extension at about 75° C. for about two minutes. To insure the elongation and renaturation is complete, the mixture after the final cycle is preferably held at about 60° C. for about five minutes.

The product double-stranded cDNA may be separated from the mixture, for instance, by gel-electrophoresis using agarose gels. However, if desired, double-stranded cDNA may be used in unpurified form and inserted directly into a suitable cloning or expression vector by conventional methods. This will be particularly easy to accomplish if the primers include restriction enzyme recognition sites.

Figure 1:
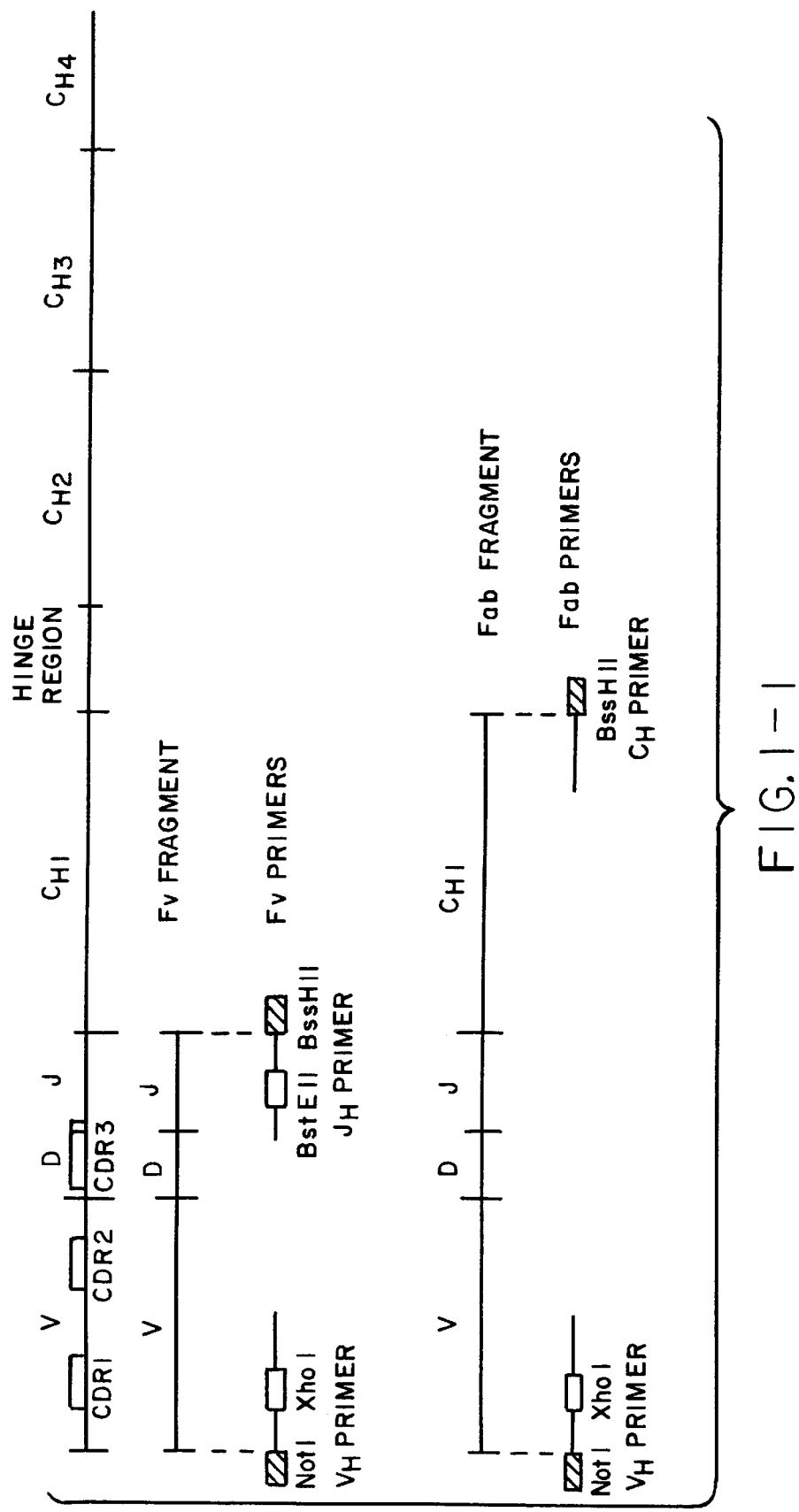
Figures 1, 2:
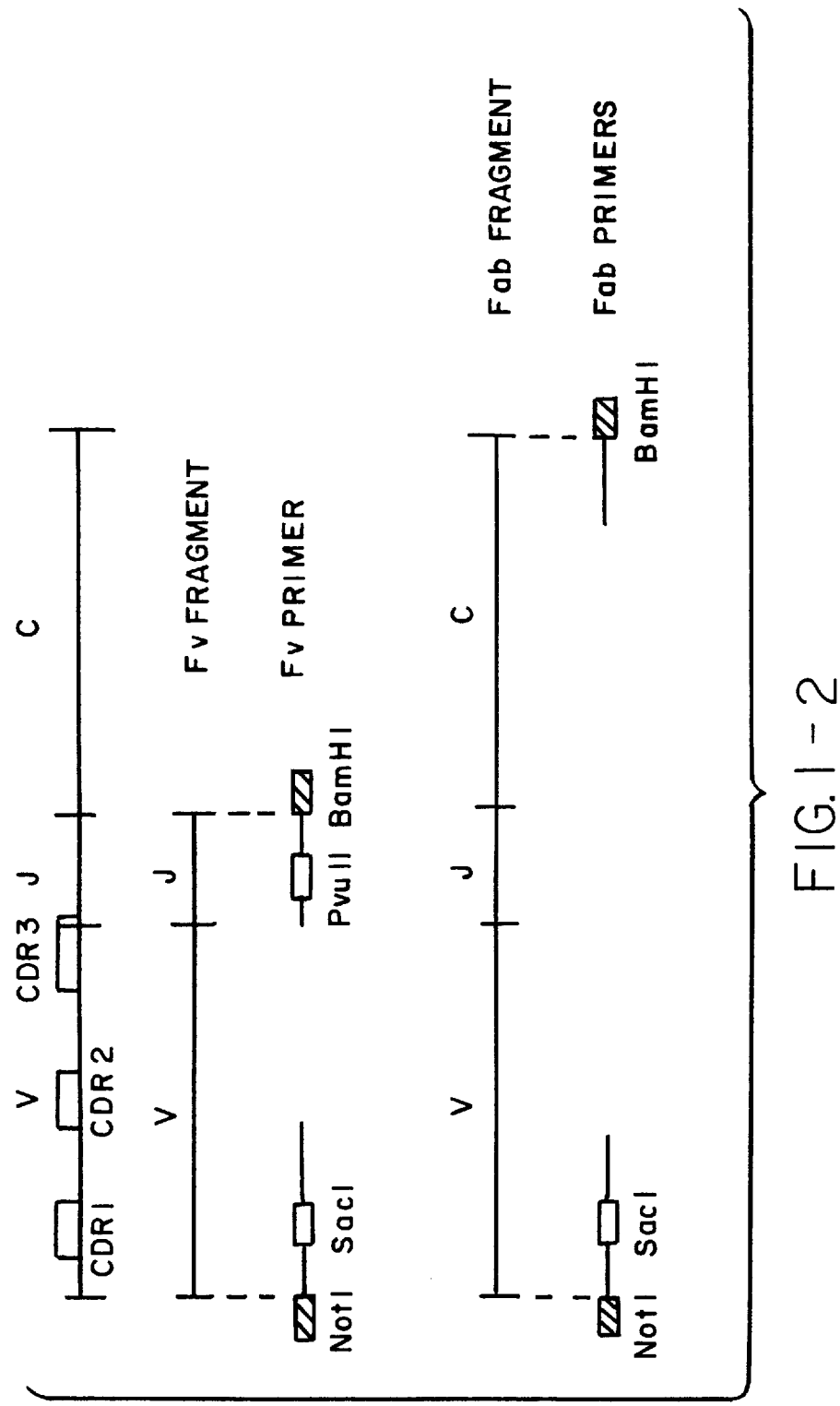
Figure 2:
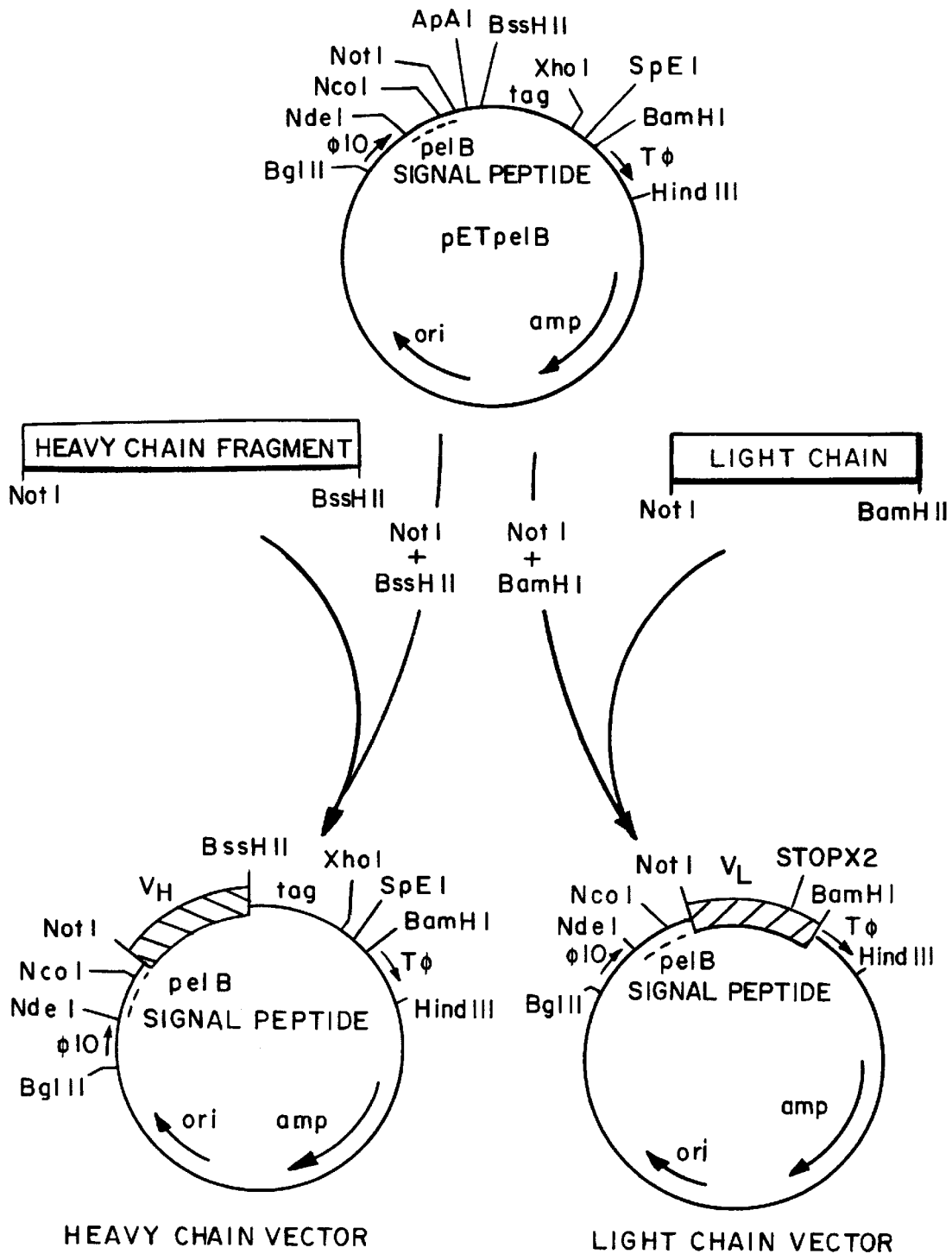

The amplified $V_H$ and $V_L$ fragments can be cloned separately into a vector designed for bacteria expression of these sequences, such as the pETpelB plasmid. See FIGS. 2 and 3. The pETpelB vector is shown in FIG. 2, with the φ10 promoter (for T7 RNA polymerase) and the Tφ transcription termination signal derived from the T7 bacteriophage [Rosenberg, et al., Gene, 56:125–135 (1987)]. The signal sequence, including the signal peptide cleavage site [Lei, et al., J. Bact., 169:4379–4383 (1987)], is designated "pel B signal peptide" and is fused onto the amino terminus variable genes cloned into Nco I (or Not I) site. Immediately upstream of the pel B signal sequence is a ribosome binding site for translation in E. coli. Fused onto the carboxyl terminus of some proteins expressed by this vector are the "tag" sequences, a small peptide derived from angiotension I which is recognized by anti-tag serum [Ward, et al., Nature, 341:544–546 (1989)]. Cloning of heavy chain genes into the vector utilizes Nco I (or Not I) and BssH II sites from the PCR primers, while the light chain cloning utilizes the same Nco I (or Not I) and a 3'BamH I site. Note that, using this strategy, only the heavy chains are fused to the tag sequence.

Amp=ampicillinase gene; or=E. coli origin or replication. Not every segment is drawn to scale for ease of representation.

Figures 1, 3:
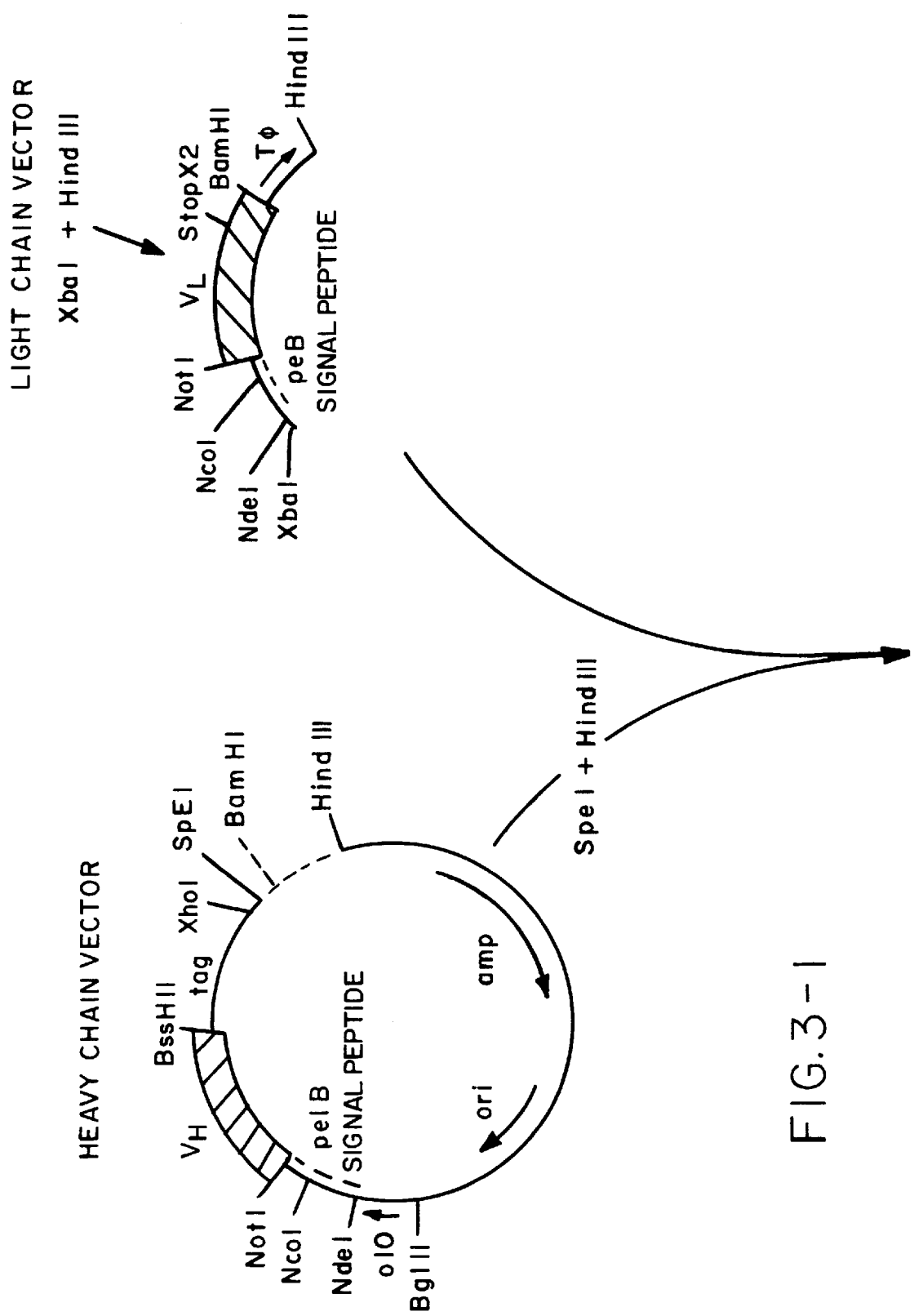
Figures 2, 3:
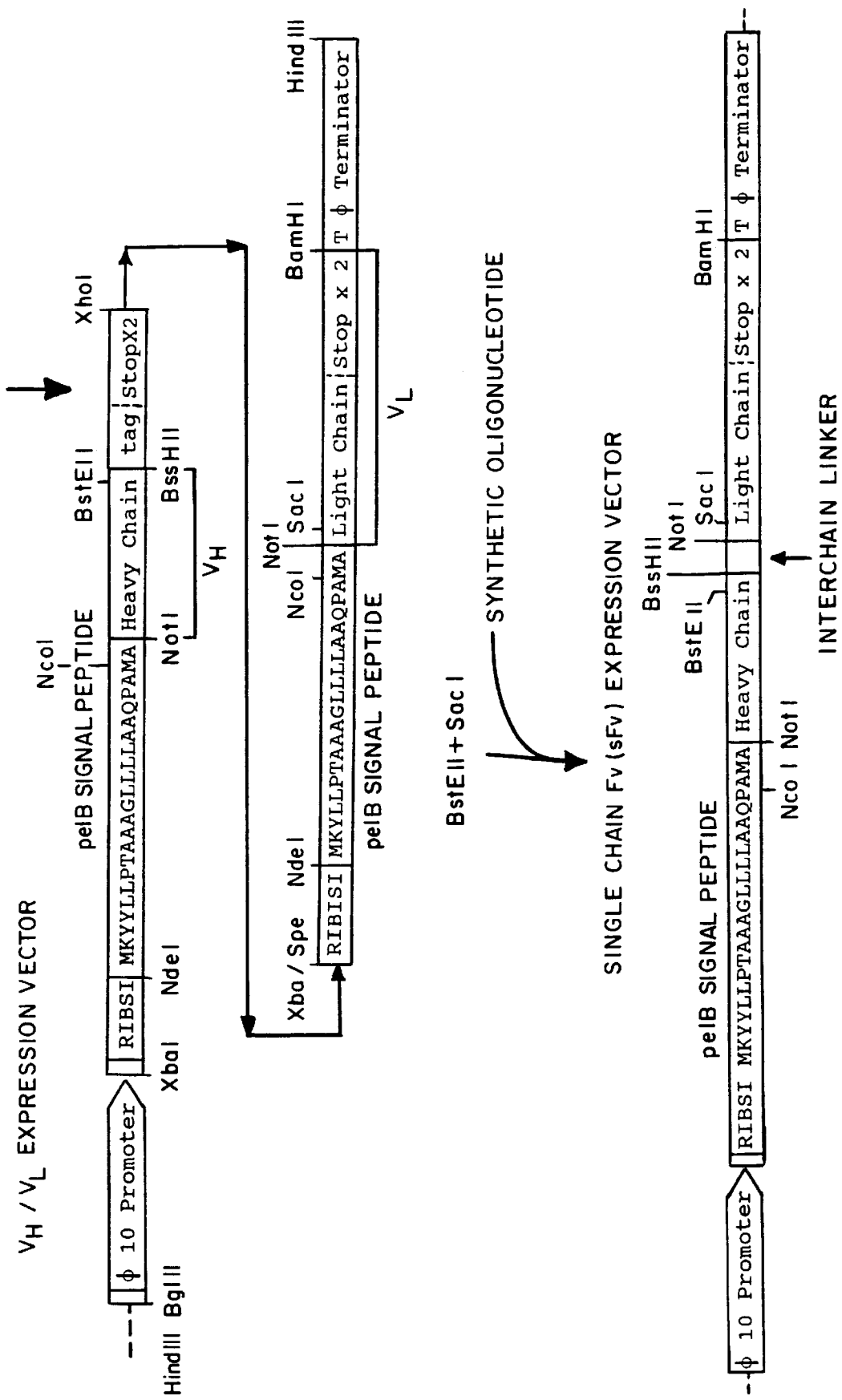

The features of this plasmid relevant to bacterial expression of antibody gene fragments are discussed below. For cloning purposes, the pETpelB vector contains a unique 5' Not I site and unique 3' sites (BssH II for $V_H$ or BamH I for $V_L$ genes). When using this plasmid, it is preferable that the PCR amplified genes are purified from low melting agarose gels following digestion with Not I and BssH II (or BamH I) and cloned into the vector. To obtain the DNA sequence of the cloned variable region sequences, oligonucleotides complementary to vector sequences flanking the insert are used as primers for dideoxy DNA sequencing [Sanger, et al., PNAS, 74:5463–5467 (1977)]. The sequence of both strands of the plasmid insert can be determined for three independent clones to minimize sequencing errors or PCR artifacts. FIG. 3 shows strategies for $V_H$ and $V_L$ expression, and construction of a single chain Fv expressor. The XbaI-Hind III fragment from the light chain expression vector (in FIG. 2) is cloned into the Spe I-Hind III digested heavy chain vector, since the Xba I and Spe I leave compatible 5' overhangs. Thus, a single plasmid can be used to express both heavy and light chains in a single bacterium, using a dicistronic message. RIBISI=ribosomal binding site. To create a single chain Fv (sFv) expressor, the $V_H/V_L$ expression vector is digested with BstE II and Sac I, which cut within the 3' end of the heavy chain gene and the 5' end of the light chain gene, respectively. Insertion of a synthetic linker reconstitutes the 3' end of $V_H$ and the 5' end of $V_L$ and allows the two chains to be joined by a flexible linker peptide (Gly-Gly-Gly-Gly-Ser)$_3$ (SEQ ID NO:5). Thus, a single protein containing the pel B signal sequence, $V_H$ segment, linker peptide and $V_L$ segment is synthesized under the control of the φ10 promoter.

Muteins may be prepared by this method also. For example, this may be achieved by using a mixture of related oligonucleotide primers as at least one of the primers. Preferably, the primers are particularly variable in the middle of the primer and relatively conserved at the 5' and 3' ends. Preferably, the ends of the primers are complementary to the framework regions of the variable domain, and the variable region in the middle of the primer covers all or part of a CDR. Preferably, a forward primer is used in the area which forms the third CDR. If the method is carried out using such a mixture of oligonucleotides, the product will be a mixture of variable domain encoding sequences. Changes in the sequence may be introduced by incorporating some mutagenic nucleoside triphosphate, so that point mutations are scattered throughout the target region. Alternatively, point mutations are introduced by using a large number of cycles of amplifications, so errors due to the natural error rate of the DNA polymerase are amplified, particularly by using high concentrations of nucleoside triphosphates. As will be discussed below, such muteins can be screened to see whether they increase the binding affinity of the antibody expressed or affect the neutralizing ability of the antibody when compared to a standard Mab, e.g., the rF105 Mab.

An expression vector with the DNA segment of the present invention can readily be made. For example, when the DNA segment is double-stranded cDNA it may be cloned directly into an expression vector. The host may be procaryotic or eukaryotic, but is preferably bacterial. Preferably, the choice of restriction sites in the primers and in the vectors, and other features of the vectors will allow the expression of functional immunoglobulins or fragments thereof. For example, in the expression of the mutein genes, the primers would be chosen to allow cloning of target sequences including at least all three CDR sequences. The cloning vector would preferably encode a signal sequence (for secretion), and sequences encoding the N-terminal end of the first framework region, restriction sites for cloning and the C-terminal end of the last (fourth) framework region, wherein all sequences are preferably connected. The DNA segment is linked to a promoter to permit expression.

A heavy chain variable domain can be expressed either as an individual domain or, if it is expressed with a complementary light chain variable domain, as an antigen binding site. Preferably, the two chains are expressed in the same cell, or secreted from the same cell, and the proteins allowed to associate non-covalently to form an Fv fragment.

The two genes encoding the complementary partners can be placed in tandem and expressed from a single vector, wherein the vector has two sets of restriction sites.

Preferably, the genes are introduced sequentially: for example the heavy chain variable domain can be cloned first and then the light chain variable domain. Alternatively, the two genes are introduced into the vector in a single step, for example, using the polymerase chain reaction to paste together each gene with any necessary intervening sequence by the methods described herein and in light of Ian and Freed, *Hybridoma Technology in the Biosciences of Medicine*, 103–115 (1985).

The two chains can also be expressed as a linked protein to produce a single chain Fv fragment (sFv), using similar vectors as described above, for example, pETpelB. As a further alternative, the two genes may be placed in two different vectors, for example, in which one vector is a phage vector and the other is a plasmid vector.

The clone sequence may also be inserted into an expression vector so that it can be expressed as a fusion protein. The variable domain encoding sequence may be linked directly or via a linker sequence to a DNA sequence encoding any protein effector molecule, such as a toxin, enzyme, label or other ligand. The variable domain sequences may also be linked to proteins on the outer side of bacteria or phage.

Successfully transformed cells can be identified by any suitable well-known technique for detecting the binding of an immunoglobulin to an antigen. Preferred screening assays are those with a binding of the antigen by the immunoglobulin produces a detectable signal, either directly or indirectly. Such signals include, for example, the production of a complex, formation of a catalytic reaction product, and the release or uptake of energy, or the like.

Once the DNA sequences from both the heavy and light chains are obtained the detailed genetic analysis of $V_H$, D, $J_H$ and $V_\kappa$ $J_\kappa$ rearrangement can be done. The subgroup classification of the heavy and light chains can be made by comparing the sequences to those available in a databank, for example the Kabat database [Kabat, et al., supra]. The identifiable germline variable region gene used in the formation of the rearranged complete $V_H$ gene can be determined. Also, the D region gene and the family of J region genes which were selected can be identified.

The cloning of the $V_H$ and $V_L$ genes into an expression vector, for example, pETpelB, allows for the expression of functional antibody fragments in bacteria. The pETpelB vector has been designed by the present inventors, and is derived from the pET vector obtained from Dr. F. William Studier (Brookhaven National Laboratory) [Rosenberg, et al., supra]. These vectors are both derived from the pBR322 plasmid, contain the bacterial origin of replication and ampicillin resistance gene and are capable of expressing a wide variety of DNAs from prokaryotic and eukaryotic sources. See FIG. 2. Transcription is controlled by the strong φ10 promoter for T7 RNA polymerase and the Tφ transcription terminator. The *E. coli* strain used for expression, BL21, contains a lysogenic bacteriophage DE3, which contains the T7 RNA polymerase gene under the control of the lacUV5 promoter and a lac i repressor. When isopropyl-B-D-thiogalactoside (IPTG) is added to the BL21(DE3) lysogen, induction of the lacUV5 promoter and high levels of T7 RNA polymerase expression result. These high levels of T7 RNA polymerase expression in turn direct a high level of transcription of the gene of interest under the control of the φ10 promoter [Rosenberg, supra].

A sample of plasmids pETpelBTAG F105 Fab and pETpelB F105 sFV were deposited at the American Type Culture Collection (ATCC), 12301 Parklawn Drive, Rockville, Md. 20852 under the terms of the Budapest Treaty on Feb. 11, 1992 and Feb. 20, 1992, respectively and were accorded ATCC Accession Nos. 75209 and 75208, respectively.

Using an expression vector such as pETpelB, the $V_H$ and $V_L$ genes can be expressed from independent transcription units. In addition, both $V_H$ and $V_L$ proteins can be synthesized as a fusion protein with the amino terminus derived from the signal sequence of the pel B protein, including the signal monitoring of Fab or Fv production in the bacterial extracts. The "tag sequence" (DRVYIHPFHL (SEQ ID NO:6)) is derived from human angiotension I and is recognized by a commercially available high-titer antiserum (Peninsula Labs, Inc.).

When the PCR amplified $V_H$ and $V_L$ genes are cloned into the pETpelB vectors as illustrated in FIG. 2 and described above. Ligation of the V genes at the 5' Not I site results in the genes being positioned in-frame with the coding sequence for the pel B signal peptide, thus allowing export of the recombinant products [Lei, et al., supra]. As shown in FIG. 1, the use of different reverse 3' primers allows for production of either Fv or Fab recombinant fragments. The primers for Fv fragment production are described above, while the reverse primers for Fab fragment production can be designed to include the constant regions just amino-terminal to the hinge region. Once cloned individually, the genes for the pel B signal-$V_H$-tag and pel B signal-$V_L$ fusion proteins can be introduced into a single plasmid, so that they can be expressed in a single bacterium by use of a dicistronic message. See FIG. 3. [Skerra and Pluckthun, *Science*, 240:1038–1041 (1988); Huse, et al., supra; Glockshuber, et al., supra].

The orientation of the $V_H$ and $V_L$ genes in the expression system also provides an easy way to synthesize single-chain Fv fragments (sFv) in bacteria. The production of sFv fragments allows efficient and durable association of the $V_H$ and $V_L$ fragments, which are joined by an interchain linker, for instance (Gly-Gly-Gly-Gly-Ser)$_3$ (SEQ IO NO:5) designed to allow maximum flexibility. This linker has been used to connect the carboxyl end of the $V_H$ fragment to the amino terminus of the $V_L$ fragment of several unrelated antibodies without apparent change in binding affinity for the antigen [Huston, et al., *PNAS*, 85:5879–5883 (1988); Glockshuber, et al., supra]. Any linker can be used so long as it does not interfere with the resultant antibody. Other universal interchain linkers have worked in an orientation in which the carboxyl terminus of the $V_L$ chain is joined to the amino terminus of the $V_H$ chain [Bird, et al., *Science*, 242:423–426 (1988)]. By deleting the BstE II-Sac I fragment from the pETpelB. plasmid expression both $V_H$ and $V_L$ chains and replacing it with a synthetic DNA fragment, a single-chain Fv fragment containing the interchain linker can be produced. See FIG. 3.

Fab, Fv or sFv fragments can be secreted into the bacterial periplasm or, at a slower rate, into the medium [Skerra and Pluckthum, et al., supra; Huse, et al., supra; Glockshuber, et al., supra; Bird, et al., supra; Huston, et al., supra]. Affinity columns containing antigen or antibodies directed against the tag sequence (or interchain linker, in the case of sFv) can be used to obtain purified antibody fragments. For example, an HIV-1 gp120 glycoprotein, in a form active for CD4 binding, is commercially available (American BioTechnology, Inc. or Celltech, Ltd.) and can be readily incorporated into an affinity column. In the latter case, it is important to use methods shown to preserve the ability of matrix-bound gp120 to absorb broadly-reactive neutralizing activity from patient serum [Haigwood, et al., supra].

Bacterially produced Fab, Fv or sFV fragments can be tested for binding affinity for gp120, compared with the purified monoclonal antibody, to determine whether mutations that might have resulted from PCR amplification or the particular constructions used altered binding affinity. Obviously, those mutations that reduced binding affinity would not be used. Affinity can be measured using gp120 obtained from American Biotechnology, Inc. or Celltech, Ltd. and iodinated using the Bolton-Hunter method [McCarthy and Markowitz, *Clin. Chim. Ata*., 132–277–286 (1983)]. Equilibrium binding measurements utilizing immunoprecipitation techniques [Huston, et al., supra] or multicavity microdialysis chambers [Skerra and Pluckthum, supra] to separate bound and free gp120 can be employed, and association constants calculated, for example from Scatchard or Sips plots [Scatchard, et al., *Ann. N.Y. Acad. Sci*., 51:660–672 (1949); Smith, et al., *Biochemistry*, 9:331–337 (1970)]. In addition, gp120 conjugated to horseradish peroxidase (HRP) or to FITC is available from American Biotechnology, Inc. These molecules also retain CD4 binding ability and are utilized to establish a semi-quantitative solid-phase ELISA to assess antibody fragment-gp120 binding.

If desired, the gene coding for the immunoglobulin or a sufficient fragment thereof to neutralize HIV isolates and/or effect CD4 binding by HIV gp120 can be mutated to improve the properties of the expressed domain, for example to increase the affinity or specificity of the antibody or their neutralizing ability. Such mutations can include single point mutations, multiple point mutations or more extensive changes and can be introduced by any of a variety of recombinant DNA methods, for example gene synthesis, site directed mutagenesis or the polymerase chain reaction.

The particular expression plasmid to be used for mutagenesis depends upon whether the antibody fragment to be modified is an Fab, an Fv or an sFv fragment. The choice of which antibody fragment is utilized depends on measurements of relative affinity for gp120 discussed above. Should the sFv fragments exhibit affinity at least comparable to the monoclonal antibody, as in the case for known examples [Huston, et al., supra; Ward, et al., supra; Glockshuber, et al., supra], these can be employed for mutagenic studies. Otherwise, it is preferable Fab or Fv fragments be used for site-directed mutagenesis.

The vector chosen for mutagenesis and phenotypic analysis preferably contains an *E. coli* origin of replication (Col E 1) and an ampicillinase gene or other antibiotic marker. The expression plasmid should also preferably contain an f1 phage origin, allowing rescue of single-stranded DNA via helper phage (M13) infection. The gene to be mutagenized can be placed under the control of a T7 RNA polymerase-dependent promoter such as the $\phi 10$ promoter described above. This allows IPTG-inducible expression of wild-type or mutant antibody fragments in the BL21(DE3) host. An expression vector with these desired features can readily be made by cloning an f1 phage origin onto the plasmids shown in FIG. 3. Alternatively, the transcription units from the latter plasmids can be cloned into the pBluescript plasmid (Stratagene) [Helseth, et al., *J. Virol*., 64:2416–2420 (1990); Olshevsky, et al., supra; Kowalski, et al., *PNAS*, 86:3346–3350 (1989)]. The pBluescript plasmid has the IPTG-inducible lac Z promoter/operator (under the control of the lac i repressor) and the T3 RNA polymerase promoter oriented upstream of a multiple cloning site. To mutagenize Fv or Fab fragments, the $V_H$ and $V_L$ segments can be positioned on separate transcription units, or produced using a dicistronic message.

In one embodiment, two methods for antibody fragment expression and determination of gp120-binding ability are tried using the wild-type antibody gene, so that the practicality and suitability of these methods can be compared. For example, the first method uses an ELISA method to detect gp120 binding to immobilized antibody. First, ELISA plates are coated with anti-tag or anti-Fab antibodies. Commercially available goat and rabbit anti-human Fab antibodies can be used to determine whether they recognize the recombinant wild-type protein. Using conditions in which the sFv is bound to the supporting antibody in the presence of, for example 0.25M urea, sFv fragments can be as effective as Fab fragments in detecting soluble antigen. Bacterial periplasmic extracts or supernatants, preferably after partial purification are bound to the immobilized antibody. Horseradish peroxidase-conjugated gp120 (American BioTechnology, Inc.) can be used to detect antibody fragments capable of binding gp120. Extracts derived from bacteria expressing irrelevant antibody fragments (e.g., anti-tat Fv) can be used as a control.

A second method utilizes in vitro transcription-translation systems for production of antibody fragments [Cohen, et al., *Nature*, supra; Salfeld, et al., *EMBO J*., 9:965–970 (1990); Cohen, et al., *J. AIDS* 3:11–18 (1990)]. For the latter method, the sFv gene is expressed from one plasmid, whereas for the Fab or Fv genes, the $V_H$ and $V_L$ gene segments are positioned on separate plasmids. The pel B signal sequence is removed from these constructs since the signal peptide will not be cleaved in the in vitro translation system. The antibody gene segments can be expressed using either T7 or T3 RNA polymerase-responsive promoters. Equimolar quantities of plasmids containing the $V_H$ and $V_L$ genes (or a single plasmid containing the sFv gene) are linearized, transcribed in vitro using T7 or T3 RNA polymerase, and the RNA capped and used in an in vitro translation mix. Labelled antibody fragments can be assessed for gp120 binding ability by incubating extracts with different amounts of gp120 and precipitating the mixture with anti-gp120 antibodies. Numerous anti-gp120 polyclonal and monoclonal antibodies are available, and those shown not to compete with the monoclonal antibody of interest are employed. Alternatively, the in vitro translation mix can be utilized in an ELISA-based assay described above.

Once it has been confirmed that functional wild-type antibody fragments are expressed, single-stranded DNA is prepared and used as a template for oligonucleotide-directed mutagenesis as described by Kunkel, et al, *Meth. Enzymology*, 154:367–382 (1987). This method provides a strong selection against the non-mutagenized strand of a double-stranded hybrid DNA, allowing for a high percentage of colonies (or plaques if phage are used as a vector) that contain the desired mutation.

By synthesis of the target single-stranded DNA to be mutagenized in a dut-ung-bacterium, which allows uracil to be incorporated into the target DNA selection of muteins is favored. This uracil-containing strand is then used as a template for in vitro synthesis of a non-uracil-containing mutant strand by priming the DNA polymerase with an oligonucleotide containing the desired mutation. The resulting double-stranded DNA is transformed into a cell with uracil N-glycosylase, inactivating the wild-type uracil-containing strand. The mutated strand survives to replicate as a plasmid or phage. While preparation of a single-stranded DNA using plasmid vectors is more tedious than when M13 phage systems are used, once a stock of single-stranded DNA containing a desired segment is obtained, mutants (muteins) can be very rapidly generated.

Single stranded DNA from the antibody gene expresser plasmid can be prepared by phage rescue, annealed to the oligonucleotide primer containing the desired mutation, filled in with DNA polymerase and ligase, and used to transform E. coli. E. coli BL21(DE3) is uracil N-glycosylase-competent and expresses IPTG-inducible T7 RNA polymerase, so it may be used as a suitable host if bacterial expression is chosen for characterization of the phenotype. Individual bacterial colonies selected on ampicillin are used for plasmid DNA preparation, and the presence of the mutation confirmed by DNA sequencing. Preferably, three independently isolated clones containing the desired mutation are assessed for antibody expression and gp120 binding, to minimize the possibility of spontaneous mutations arising at a distance from the desired mutation contributing to the observed phenotype.

The gp120-binding ability of the mutant antibodies is normalized for the amount of mutant protein expressed in the bacterial extract or in vitro translation mix. If it is found that the level of expression is sufficient, Coomassie Blue or silver staining of SDS-acrylamide gels on which extracts have been run may be sufficient for quantitation. Lower levels of antibody fragment expression can be normalized by Western blotting or immunoprecipitation with anti-tag antiserum, or commercially available goat and rabbit anti-human Fab antibodies, if the latter are shown to react with the wild-type fragment. These polyclonal antibodies may prove to exhibit better reactivity to multiple epitopes on the recombinant molecules, and would circumvent the occasionally observed problem of recombinant antibody fragments losing the "tag" sequence secondary to bacterial proteolytic cleavage [Ward, et al., supra]. Once level of antibody fragment production is assessed, the gp120-binding ability of the mutant antibody fragment is determined as described for the wild-type fragment above. In the ELISA assay, the level of mutant antibody fragment recognized by the antibody used for immobilization is determined independently by immunoprecipitation, thus ensuring that differences in levels of mutant fragment bound by the immobilizing antibody are not responsible for observed decreases in gp120 binding.

Gross conformational changes in the antibody structure as a result of the mutation could account for some of the observed decreases in gp120 binding. This should not be problematic since most amino acid changes in exposed turns on proteins, such as the antibody CDR loops, exert less effect on protein confirmation than do changes in hydrophobic residues in the protein core [Creighton, "Proteins: Structure and Molecular Principals" (Freedman and Company, New York (1984)]. Finally conformation-dependent monoclonal antibodies directed against the F105 idiotype (e.g., anti-idiotypic monoclonal antibodies) can be used to assess the correctness of the mutant protein conformation.

The identification of, for example, F105 mutant antibodies that exhibit higher affinity for gp120 or have a stronger neutralizing effect, or recognize and bind to a differing range of HIV isolates would be highly desirable for therapeutic purposes and for providing critical reagents for investigating the generation of such reactiveness in vivo.

One can use a system to select for binding of antibody, e.g., sFv fragments to a selected antigen, e.g., HIV gp120, to identify desired antibodies from a starting population of greater than $10^6$ proteins [McCafferty, et al., Nature, 348:552–554 (1990)]. For example, using a system that involves the production of filamentous bacteriophage carrying fusion proteins between sFv and the viral gene III surface protein ("phage antibodies"). The gene III protein is responsible for the attachment of the phage to the F pilus of the target bacterium [Kornberg, "DNA Replication" (Freeman, San Francisco) (1980)]. However, the gene III protein can tolerate the presence of polypeptides (including sFv fragments of antibodies) inserted near the amino terminus without loss of function [Smith, et al., Science, 228:1315–1317 (1985); Parmley and Smith, Gene, 73:305–318 (1988); Scott and Smith, Science, 249:386–390 (1990); Devlin, et al., Science, 249:404–406 (1990)]. Thus, replication-competent phage displaying functional antibody variable regions on their surface can be generated. Phage containing functional antibody fragments with desirable phenotypes can be enriched by multiple rounds of affinity chromatography [McCafferty, et al., supra].

The initial step using this method is the generation of filamentous phage both suitable for high efficiency mutagenesis and expressing the wild-type sFv antibody fragment as a fusion protein with the gene III protein. The fd phage previously used to generate phage antibodies by McCafferty, et al., supra is preferably used. First, single stranded phage DNA is prepared following transfection of the fd-tet vector (American Type Culture Collection) into F' dut-ung-E. coli (e.g., CJ236, RZ1032). In vitro mutagenesis is employed [for example that of Kunkel, et al., supra] to produce unique Kpn I and Eag I sites at positions 1611 and 1631 (see FIG. 11). These changes do not affect the coding sequence of gene III. A synthetic oligonucleotide is cloned into the Kpn I/Eag I-digested fd-tet DNA to reconstitute the deleted pIII coding sequence and to insert in-frame segments of the sFv gene. These flanking segments of the sFv gene contain the Xho I and Pvu II sites within the sFv gene that allow cloning the full sFv cassette from the pET vector. The result is a fd-tet-sFv vector, which encodes a pIII-sFv fusion protein, containing (from amino terminus to carboxy terminus) the pIII protein signal sequence (including the Ser-Ala-Glu signal peptidase cleavage site), the sFv, and the remaining pIII sequences.

Phage are generated by transfection of the fd-tet-sFv vector into E. coli TG1 and subsequently propagated in these bacteria while maintaining tetracycline selection. Control phage are generated by transfection of the fd-tet plasmid. High titer phage supernatants can be polyethylene glycol precipitated and resuspended in approximately 1/100 of the original volume, followed by clearing residual bacteria and aggregated phage by centrifugation. Ability of the sFv-phage and control phage to bind gp120 are tested by ELISA, using a concentrated phage stock, as described by McCafferty, et al., supra. Briefly, gp120-coated plates are incubated with approximately $2 \times 10^{10}$ phage in phosphate-buffered saline containing 2% skimmed milk powder. Plates are washed with 0.5% Tween 20 in PBS followed by PBS, and bound phage detected by sheep anti-M13 antisera (known to cross-react with the closely related fd phage) and horseradish peroxidase-conjugated anti-sheep serum (Sigma). Bovine serum albumin-coated plates are used as controls to ascertain if any reactivity seen is specific for gp120.

Once it has been verified that a phage antibody can be produced using the wild-type sFv gene insert, a library of semi-random mutations can be selected for, for instance, higher affinity and/or specificity. Information regarding the relative contribution of each CDR loop and of specific residues within the loops to the overall binding affinity for gp120 will be available from the site-directed mutagenesis studies using a plasmid expression vector described above. The semi-random mutagenesis of the phage antibody is targeted so that these regions are selectively altered, rather than attempting to randomly mutagenize the coding sequence of an entire CDR loop. In this manner, it will take maximum advantage of the fact that the starting point is an antibody that already binds a desirable target on gp120. This increases the probability by many orders of magnitude of identifying antibodies of higher affinity, relative to an approach employing totally random CDR loops and relying on the selection procedure alone.

The alteration of the sFv gene insert is performed by oligonucleotide-directed mutagenesis, using, for instance, the Kunkel, et al., supra procedure to enrich for mutants. For mutagenesis of each CDR loop selected, a set of degenerate oligonucleotides is generated. Each set of oligonucleotides consists of n/2 batches, where n is the number of amino acids in the CDR loop selected for mutagenesis. Each batch of oligonucleotides have sequences identical to the CDR-coding region and immediate flanking framework sequences, except for degeneracy at two adjacent internal codons specifying CDR amino acids. These two codons have the sequence NNS NNS, where N is a mixture of G, A, T and C and S is a mixture of G and C. The NNS codon encodes all twenty amino acids but produces only one of the three termination codons. By using each set of oligonucleotides at a time to generate mutants, the alterations introduced can be limited to at most two amino acids at a time within a CDR loop. If initial screening indicates that the generation of mutant phage antibodies with the desired characteristics are not obtained, the randomness of the mutagenesis can be increased by:

1. simultaneously introducing different sets of oligonucleotides into the annealing reaction with the single-stranded template so that mutations affecting combinations of different CDR residues can be generated; and
2. increasing the length of the degenerate region from two to three or four codons.

The former approach may prove to be important if interactions between CDRs are required for generating high-affinity antibody fragments. This procedure using F', uracil-N-glycosylase-competent bacterial hosts (e.g., TG-1, MV1190) for phage replication, provides selection pressure so that most of the recombinant phage express mutant sFv proteins. High titer stocks of phage are grown so that phage antibodies can be screened for two phenotypes:

a) higher affinity for gp120; and
b) ability to neutralize HIV-1, HIV-2 or SIV-1 infection in vitro.

To identify mutant phage antibodies that exhibit a higher affinity for gp120 than the wild-type phage antibody several methods can be used. While affinity chromatography has been used to select phage antibodies capable of binding antigen [McCafferty, et al., supra], one preferably uses an ELISA assay for the selection of high affinity antibodies. The ELISA assay described by McCafferty, et al., supra can be modified for purposes of this selection, using the wild-type phage antibody to establish selection conditions. ELISA plates are coated with decreasing amounts of a gp120 preparation shown in previous studies to bind the antibody fragments. The wells are incubated with wild-type phage antibodies in 2% skimmed milk powder in buffer in the presence or absence of increasing concentrations of purified monoclonal antibody or Fab fragment as a competitor. Wells are then be washed stepwise with buffers of increasing pH 9.0 up to pH 9.5 with triethylamine and finally eluted with 100 mM triethylamine. Both washes and elutes are neutralized with 0.5M sodium phosphate buffer (pH 6.8) and titered on bacteria. The titration using wild-type phage antibody can indicate the minimum-stringency conditions (gp120 concentration, competing monoclonal antibody, and wash conditions) for which little or no wild-type phage antibody is detected. It is also possible to test whether, using less stringent conditions, wild-type phage antibody can be selected from a large population of control phage expressing an irrelevant sFv fragment (e.g., recognizing lysozyme [McCafferty, et al., supra]. This will ensure that the phage antibodies can be selected even when present at low concentrations in the virus stock. The selection system, using conditions where no wild-type phage antibodies are selected, are then be applied to pools of mutant phage antibodies. Selected viruses are propagated and then subjected to a second or, if necessary, a third round of selection. The number of selection rounds can be determined by the diversity of the selected population of phage antibodies. This can be determined by PCR sequencing of cloned phage in the sFv segments targeted for mutagenesis. If the diversity is high, more stringent selection conditions (increased concentrations of competing antibody, increased number of washes, decreased gp120 concentration) can be employed to select phage antibodies of maximal affinity. The sFv fragments selected can be sequenced, expressed in bacteria, and affinity for gp120 measured and compared with the wild-type sFv as described above. These higher-affinity sFv fragments can serve as starting points for mutagenesis directed at other elements of the CDR loops not targeted in the initial generation of the mutants. Multiple rounds of mutagenesis and selection, using the high-affinity mutant as the starting "wild-type" protein, might result in further affinity increases.

For some higher-affinity sFv fragments, the ability to inhibit syncytium formation can be tested. Neutralization assay employing replication-competent laboratory and wild-type HIV isolates can also be performed. For these purposes, selected sFv variants are be expressed in bacteria, which can be grown in large quantity for eventual purification by affinity chromatography using anti-tag or anti-Fab antibodies.

As a result of knowing the nucleotide sequence of one of these genes, one can screen for the presence of the antibody in mammals and quantify that level. Such a screening method can be used to diagnose and study the progression of disease in HIV-infected patients, as well as to study the immune response in trial vaccination volunteers. For example, a PCR-based assay can be used to determine the presence and amount of transcript for the antibody in a sample of patients' PBLs. Such a screening method can be carried out using 5' PCR primers from the leader peptide of both the $V_H$ 71-4 heavy chain and Humvk325 light chain genes, and non-specific 3' primers that anneal to the constant regions of the κ chain or the J region of the heavy chain. Such primers can be added to tissue or fluid, more preferably fluid. Fluid includes, for example, blood, serum, plasma, urine, cerebrospinal fluid, supernatant from normal cell lysate, supernatant from infected cell lysate, preferably, T cell lysate. The results of 30 PCR cycles of 5% of the cDNA is shown in FIG. 14.

Such a diagnostic test can be made more specific by modifying the PCR primers used. For example, the 3' primers can be made more specific by designing them to be complementary to the CDRs. For example, putting the 3' primer in the 3' end of the CDR3 allows more specific PCR amplified product to be obtained. Alternatively, the 5' primer could also be made more specific by making this PCR primer complementary to CDR1, and therefore, amplifying the DNA sequence between CDR1 and CDR3. This amplification could be performed for both heavy and light chains. The relative amount of signal, and/or the presence or absence of signal could be determined by PCR.

The antibodies of the present invention having binding activity against the gp120 epitopes of the HIV-1, HIV-2 and/or SIV and can be used to prevent or minimize infection of cells by the virus. More preferably, the antibody has binding activity against HIV-1 and/or HIV-2. Still more preferably, it has binding activity against HIV-1. Preferably, the cells are human cells. This method comprises administering a therapeutically effective amount of the antibody to a fluid or cell sample from a mammal suspected of having the virus to interfere with the viruses ability to bind to and enter a cell. Preferably, one uses a body fluid sample. Fluid includes, for example, blood, serum, plasma, urine, cerebrospinal fluid, supernatant from normal cell lysate, supernatant from infected cell lysate, preferably, T cell lysate. Preferably, the mammal is a primate, more preferably, it is a human. When used in viva for therapy, the antibodies of the present invention are administered to the patient in an amount that eliminates or reduces the ability of the virus to enter other cells. The antibody acts to block binding site of the gp120 protein and therapy reduce the viruses ability to enter a cell and reproduce.

The antibody can be delivered by any of a number of means. For example, either can be administered by parenteral injection (intramuscular (i.m.), intraperitioneal (i.p.), intravenous (i.v.) or subcutaneous (s.c.)), oral or other routes of administration well known in the art. Parenteral administration is preferred.

The amount used will typically be in the range of about 0.1 mg to about 10 mg/kg of body weight. The antibodies will preferably be formulated in a unit dosage form.

For example, solid dose forms that can be used for oral administration include capsules, tablets, pills, powders and granules. In such solid dose forms, the active ingredient, i.e., antibody or peptide, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the antibody. They can also be manufactured in a medium of sterile water or some other sterile injectable medium before use. Further examples of these vehicles include saline, Ringer's solution, dextrose solution and 5% human serum albumin. Liposomes may also be used as carriers. Additives, such as substances that enhance isotonicity and chemical stability, e.g., buffers and preservatives, may also be used.

The preferred range of active ingredient in such vehicle is in concentrations of about 1 mg/ml to about 10 mg/ml. More preferably, about 3 mg/ml to about 10 mg/ml.

These antibodies may also be used as carriers to form immunotoxins. As such, they may be used to deliver a desired chemical or cytotoxic moiety to the epitope on gp120. The cytotoxic moiety of the immunotoxin may be a cytotoxic drug or an enzymatically active toxin of bacterial, fungal or plant origin, or an enzymatically active polypeptide chain or fragment ("A chain") of such a toxin. Enzymatically active toxins and fragments thereof are preferred and are exemplified by diphtheria toxin A fragment, non-binding active fragments of diphtheria toxin, exotoxin A (from *Pseudamonas aeruginosa*), ricin A chain, abrin A chain, modeccin A chain, alphasarcin, certain *Aleurites fordii* proteins, certain Dianthin proteins, *Phytolacca americana* proteins (PAP, PAPII and PAP-S), *Momardica charantia* inhibitor, curcin, crotin, *Saponaria officinalis* is inhibitor, gelonin, mitogellin, restrictocin, phenomycin, and enomycin, Ricin A chain, *Pseudamonas aeruginosa* exotoxin A and PAP are preferred.

Conjugates of the monoclonal antibody and such cytotoxic moieties may be made using a variety of bifunctional protein coupling agents. Examples of such reagents are N-succinimidyl-3-(2-pyridyldithio) propionate (SPOP), iminothiolane (IT), bifunctional derivatives of imidoesters such as dimethyl adeipimidate HCI, active esters such as disuccinimidyl suberate, aldehydes such as glutaradehyde, bis-azido compounds such as bis(p-diazoniumbenzoyl)-ethylenediamine, diisocyanates such as tolylene 2,6-diisocyante, and bis-active fluorine compounds such as 1,5-difluoro-2,4-dinitrobenzene.

The enzymatically active polypeptide of the immunotoxins according to the invention may be recombinantly produced. Recombinantly produced ricin toxin A chain (rRTA) may be produced in accordance with the methods disclosed in PCT WO 85/03508 published Aug. 15, 1985. Recombinantly produced diphtheria toxin A chain and non-binding active fragments thereof are also described in PCT WO85/03508 published Aug. 15, 1985.

These antibodies may also be used to deliver an enzyme that will cleave the gp120 at one of these sites, and thus, delete the binding site. In another embodiment, these antibodies can be used to deliver molecule which will cap the site or an adjacent site. Any molecule that will hinder the binding of gp120 to CD4 receptors can be used.

The present invention is further illustrated by the following examples. The examples are provided to aid in the understanding of the invention and are not to be construed as a limitation thereof.

EXAMPLE I cDNA SYNTHESIS AND PCR AMPLIFICATION OF F105 IMMUNOGLOBULIN GENES FROM F105 HYBRIDOMA

The F105 hybridoma was derived by fusion of EBV transformants with the HMMA2.11TG/0 cell line, a non-secreting human-mouse myeloma analogue [Posner, et al., supra]. Total RNA was harvested from the hybridoma by the method of Chomczynaki, et al. [*Analytical Biochemistry*, 162:156 (1987)]. First strand cDNA was synthesized in a 25-ul reaction from 5 ug of total RNA by using oligo(dT) priming and the Moloney murine-leukemia virus reverse transcriptase (400 U) according to the methods of Gubler, et al., [supra]. Five to ten percent of the first strand cDNA was used to perform the PCR reactions. The temperatures used for the PCR were: Melt 94° C., 1 min.; primer anneal 52° C., 2 min.; primer extension 72° C., 2 min. One min. ramp times were used except a 2 min. ramp time was used between annealing and extension. Ethidium bromide stained 2% agarose gels were used to separate the PCR fragments. The appropriate band was excised, gene cleaned (Bio 101, La Jolla, Calif.), Klenow repaired, restriction enzyme digested and cloned into pSL1180 (Pharmacia LKB Biotech. Inc., Piscataway, N.J.) using SURE bacteria (Stratagene, La Jolla, Calif.) as hosts. At least three separate transformants were sequenced by the method of Sanger, et al., supra using both forward and reverse sequencing primers to minimize sequencing and PCR artifacts. The nucleotide sequence is set out in the sequence listing as SEQ ID NO:1 and SEQ ID NO:3. The sequencing primers were designed to be complementary to the polylinker sequences of pSL1180.

The heavy chain pair consists of a $V_H$ primer and a $J_H$ or $C_{H1}$ primer, each containing convenient restriction sites for cloning. The Kabat database on immunoglobulins was used to analyze the amino acid and codon distribution found in the six distinct human $V_H$ families [Kabat, et al., supra]. Based on this analysis, the 35 base pair universal 5' $V_H$ primer was designed, TTTGCGGCCGCTCAGGTGC-ARCTGCTCGAGTCYGG (SEQ ID NO:7) that is degenerate for two different nucleotides at two positions and will anneal to the 5' end of FR1 sequences. A 5' Not I site (left-underlined) has been introduced for cloning the amplified DNA and is located 5' to the first codon of the $V_H$ gene. An internal Xho I site has been introduced as well (right-underlined). Similarly, a $J_H$ region oligonucleotide was designed for reverse priming at the 3' end of the heavy chain variable gene, TTAGCGCGCTGAGGTGACCGTTGAC-CRKGGT (SEQ ID NO:8). Based on the nucleotide sequence of the six human $J_H$ region minigenes, this primer contains two degenerate positions with two nucleotides at each position. A BssH II site (left-underlined) 3' to and immediately adjacent to the codon determining the last amino acid of the J region allows convenient cloning at the 3' end of the $V_H$ gene. An internal BstEII site (right-underlined) was introduced as well. To obtain unbiased sequence data in the $J_H$ region, a reverse $IgG_1$ $C_{H1}$ primer was designed which terminates just 3' of the first cysteine codon in the hinge exon, TTAGCGCGCACAA-GATTTGGGCTC (SEQ ID NO:9) [Kabat, et al., supra]. A BssH II site was similarly introduced for cloning. The resulting gene product (H fragment) was intended to correspond to a Fd of $IgG_1$ isotype and conserves the H-L disulfide bond [Mullinax, et al., *PNAS*, 87:8095–8099 (1990)]. A primer corresponding to amino acids 183 to 189 of $IgG_1$ $C_{H1}$ region was used for DNA sequencing, TGCT-GAGGGAGTAGAGT (SEQ ID NO: 10).

A similar strategy was used to design PCR primers for the human$_\kappa$ chain variable genes. There are four families of human $V_\kappa$ genes. The 5' $V_\kappa$ primer TTTGCGGCCGCT-GAGCTCSWGMTGACCCAGTCTCCA (SEQ ID NO: 11), which anneals to the 5' end of the FR1 sequences, is degenerate at three positions (two nucleotides each) and contains a Not I (left-underlined) site at a position similar to that of the $V_H$ region. An internal Sac I site was also present (right-underlined). The reverse 39 base pair $J_\kappa$ primer CGAGGATCCTTATTAACGCGTGATCTC-CASYTTGGTCCC (SEQ ID NO: 12), designed from the sequence of five human $J_\kappa$ minigenes, was degenerate at three positions (two nucleotides at each position) and contains an internal Mlu I site (right-underlined) immediately flanking the $J_\kappa$ coding region and is then followed by two stop codons and a BamH I cloning site (left-underlined). To obtain unbiased sequence data in the $J_\kappa$ region, two reserve κ constant region primers were designed. The first primer, CGAGGATCCTTATTAACGCGTTGGTGCAGCCAC AGT (SEQ ID NO: 13) will anneal to the most 5' end of the κ constant region and has a similar flanking sequence arrangement as the $J_\kappa$ primer. A second primer, TGGG-GATCCTTATTAACACTCTCCCCTGTTGAA (SEQ ID NO: 14) was designed to anneal to the most 3' κ constant region nucleotides and this region was followed by two stop codons and a BamH I cloning site.

After the primary nucleotide sequence was determined for both the F105 heavy and κ chain genes and the germ line genes were identified, PCR primers were designed based on the leader sequences of the $V_H$ 71-4 [Lee, et al., supra] and Humvk325 [Radoux, et al., *J. Exp. Med.*, 164:2119–2124 (1986)] germ line genes. The $V_H$71-4 leader primer TTTAC-CATGGAACATCTGTGGTTC (SEQ ID NO: 15) and the Humvk325 leader primer GGAACCATGGAAAC-CCCAGCGCAG (SEQ ID NO: 16) both contain a 5' Nco I site (underlined). These leader primers were used in conjunction with the respective C region primers for PCR amplification experiments.

EXAMPLE II

CLONING AND EXPRESSION OF F105 Fab ANTIBODY

The F105 Fab fragment was cloned into the pETpelB expression vector using the same protocol as in Example I. For PCR amplification, the heavy chain hinge primer and the most 3' κ region primers were used as the 3' primers. See FIG. 1. The 5' primers were the same as used in Example I. The PCR amplification products were obtained under the same annealing and PCR conditions as in Example I.

The pETpelB vector has a φ10 promoter (for T7 RNA polymerase) and the Tφ transcription termination signal derived from the T7 bacteriophage [Rosenberg, et al., supra]. The signal sequence, including the signal peptide cleavage site [Lei, et al. supra], is designated in FIG. 2 "pelB signal peptide" and is fused onto the amino terminus of variable genes cloned into Nco I (or Not I) site. Immediately upstream of the pel B signal sequence is a ribosome binding site for translation in *E. coli*. Fused onto the carboxyl terminus of some proteins expressed by this vector are the "tag" sequences, a small peptide derived from angiotension I which is recognized by anti-tag serum [Ward, et al., supra]. Cloning of heavy chain genes into the vector utilizes Nco I (or Not I) and BssH II sites from the PCR primers, while the light chain cloning utilizes the same Nco I (or Not I) and a 3'BamH I site. Using this vector, only the heavy chains are fused to the tag sequence.

For cloning of the F105 heavy chain, the PCR products were purified on a 2% low melting point agarose gel. The appropriate band was excised, restriction enzyme digested with Not I and BssH II and cloned in vector pETpelB which had been digested with Not I and BssH II, thus yielding a heavy chain vector. See FIG. 2.

The resulting plasmid was used to transform SURE bacteria (Stratagene, La Jolla, Calif.). The proper inserts were confirmed by digestion of plasmid mini preps of individual colonies with the restriction enzymes used for cloning.

For cloning the F105 light chain, the same procedure was used, however, the PCR products were digested with Not I and BamH I and cloned in vector pETpelB which had been digested with Not I and BamH I to yield a light chain vector. See FIG. 2. The light chain vector was digested with Xba I and Hind III to obtain a light chain fragment containing appropriate flanking sequences. See FIG. 3.

Next, the heavy chain vector was digested with SpaI and Hind III, and ligated with the light chain fragment. Because the Xba I and Spa I have cohesive ends, this allowed for the creation of a dicistronic message. The resulting vector was then transformed in to SURE bacteria to confirm that the dicistronic cassette had been properly cloned.

The resulting plasmid was transformed into BL21 (DE3) and cultured under appropriate conditions at 37° C., after reaching O.D.$_{600}$ of 0.6 the cells were induced with 1 mM IPTG (control-no IPTG). Bacteria were harvested after a 2 hour incubation at 37° C. As shown in FIG. 4, expression of F105 Fab antibody fragment (rF105 Fab) in BL21(DE3) is readily documented following IPTG induction, both by Coomassie Blue staining of SDS-acrylamide gels (FIG. 4A) and on Western blots (FIG. 4B and FIG. 4C). For protein detection, total cell lysates were separated on 12.5% SDS-polyacrylamide gels. Coomassie Blue staining of the total cell extracts show the appearance of two protein bands at 22 and 25 kD which corresponds to the $V_L$ and $V_H$-tag fusion protein, respectively. For Western blots, either rabbit anti-$V_H$4-FR1 (Silverman, et al., *Eur. J. Immunol.*, supra], an antisera against a $V_H$IV framework peptide followed by Vector Labs immunodetection kit using alkaline phosphatase as enzyme. High levels of $V_H$ protein were induced in this plasmid/host system only after induction with IPTG. No specific proteins were detected in the Western blots of control BL21(DE3) bacteria containing the pETpelB vector with no $V_H$ gene insert, even after IPTG induction [data not shown]. Rabbit anti-angiotension (anti-tag) when used as a primary antibody gave the identical results [data not shown]. Panel C of FIG. 4 shows a Western blot of F105 $V_L$ protein probed with goat anti-κ chain antibody (Southern Biotechnology Associates). In both panels, the upper band represents precursor protein prior to pel B signal cleavage.

Figure 5:
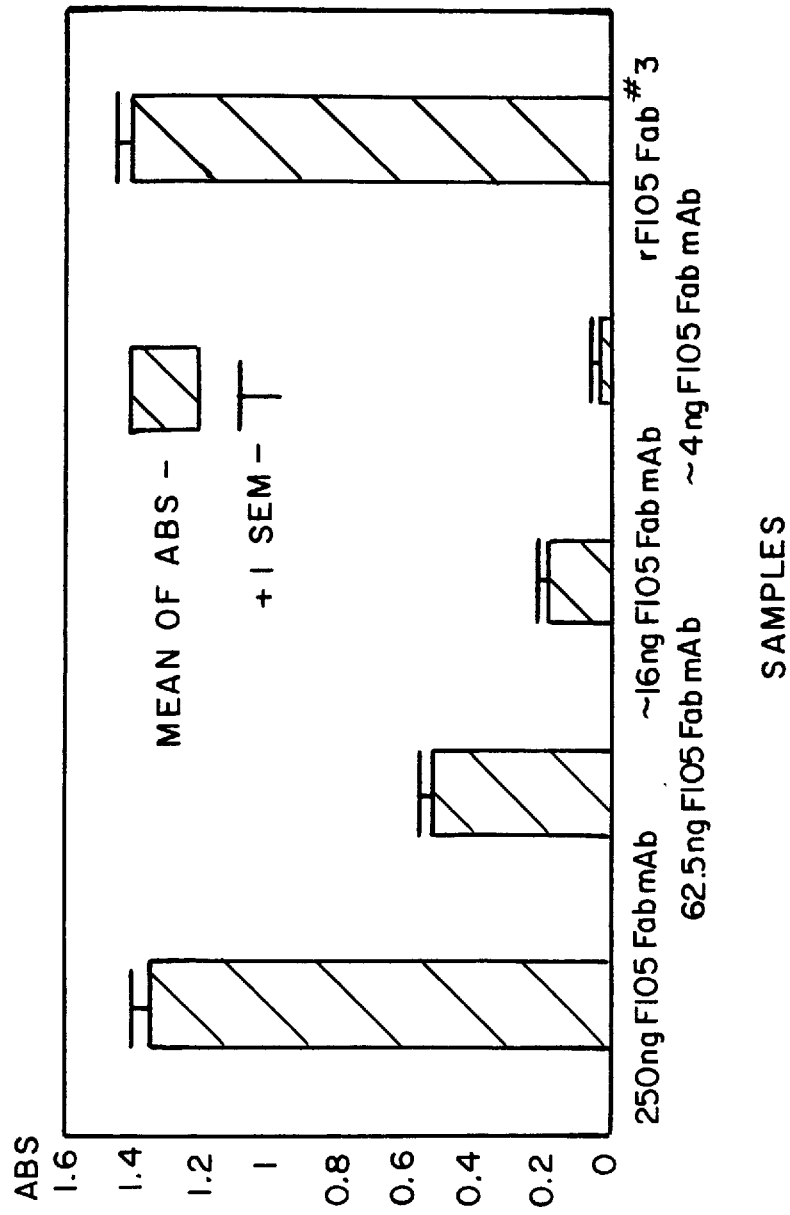

FIG. 5 shows the detection of gp120 binding activity with rF105 Fab produced in BL21(DE3). Two hours after induction with 1 mM IPTG, a periplasm sub-cellular fraction was obtained from BL21(DE3) transformed with pETpelB tag vector containing the F105 Fab cassette. Concentrated samples of the periplasm fractions were then incubated on rgp120 coded ELISA plates (American Biotechnology, Inc., Cambridge, Mass.). Binding of both F105 Fab (produced by papain cleavage) and rF105 Fab to gp120 was detected with goat anti-κ chain antibody followed by immuno-detection using alkaline phosphatase as enzyme.

Figure 6:
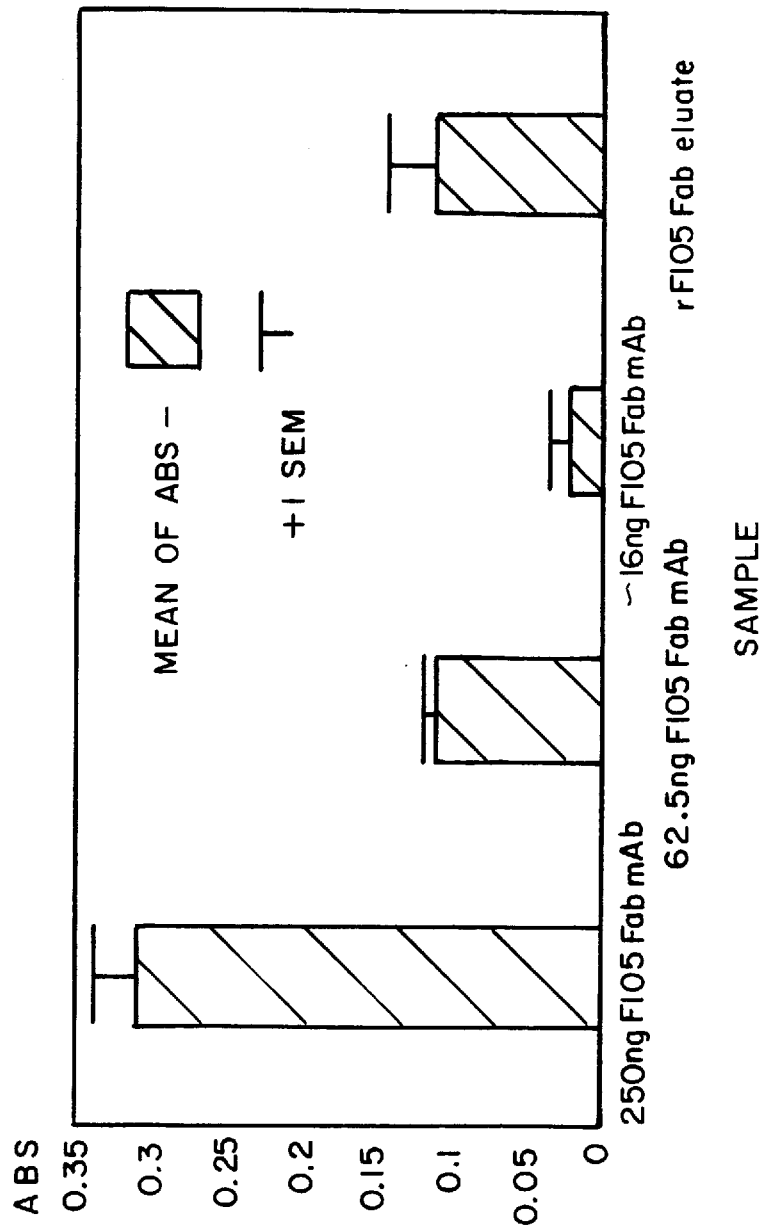

FIG. 6 shows the results an affinity column purification of rF105 Fab antibody fragments. Periplasm preparations of BL21(DE3) transformed with pETpelB tag vector containing the F105 cassette were passed through a gp120 affinity column. Bound rF105 Fab was eluted with glycine-HCL (pH 2.6) followed by neutralization with 1M Tris-HCL (pH 8.0). The pooled fractions were then analyzed by ELISA on gp120 coded plates as discussed above.

EXAMPLE III

CLONING AND EXPRESSION OF F105 SINGLE CHAIN Fv (sFV)

To clone the F105 single chain Fv, the 5' tails of the reverse $J_H$ primer and the forward $V_K$ PCR primers were designed to have 45 nucleotides perfectly complementary to one another and encoding for the interchain linker sequence $(Gly_4-Ser)_3$. The primers are set out in Table 1.

An internal interchain linker restriction site BspE I was also introduced and the $J_H$ and $V_K$ linker boundaries contained PstE II and Sac I sites to facilitate future cloning.

Annealing conditions were established to allow amplification of the F105 heavy chain and light chain with these extension arms. These conditions only involved chaining the annealing temperature to 50° C. The heavy and light chains were separately amplified by PCR, the PCR products were digested, the heavy chain PCR product was digested with Not I and BspE I and the light chain product was digested with BspE I and Xba I. These two products were cloned in a 3-piece ligation with the plasmid vector, pSL1180 which had been digested with Not I and Xba I.

Figure 8:
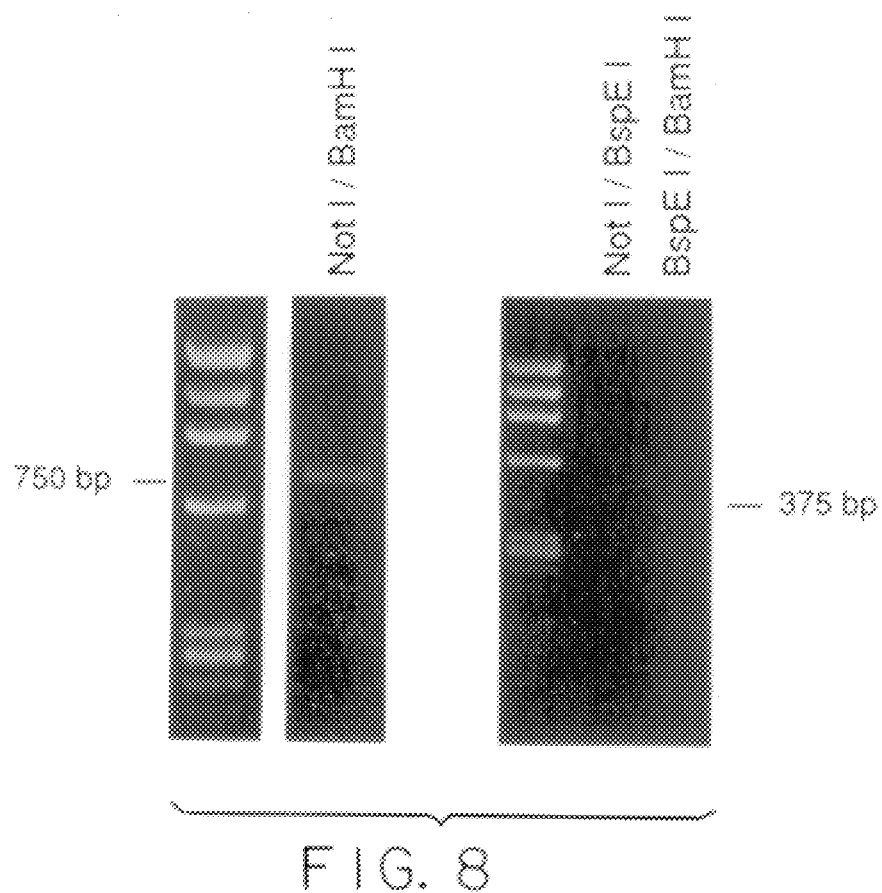
Figure 12:
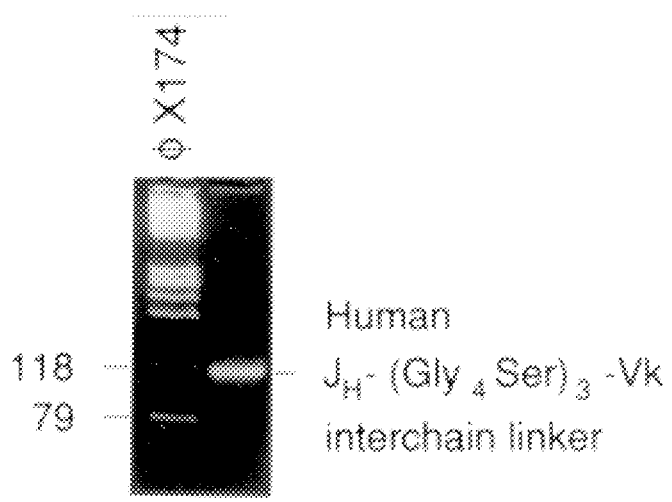
FIG. 12 shows PCR amplification of F105 sFv derived interchain linker containing 5' flanking sequences from $J_H$ and 3' flanking sequences from $V_\kappa$.

FIG. 8, left panel shows that successful cloning of the F105 sFv was achieved. This was confirmed by digestion with Not I/BspE I (heavy chain) and BspE I/Xba I (light chain) (FIG. 8, right panel, FIG. 8A). This Fv single chain antibody construct was removed by restriction enzyme digestion and cloned directly into the pETpelB expression vector. The resulting plasmid was used to transform BL21 (DE3) for expression of the F105 single chain Fv.

Figures 9A, 9B, 9C:
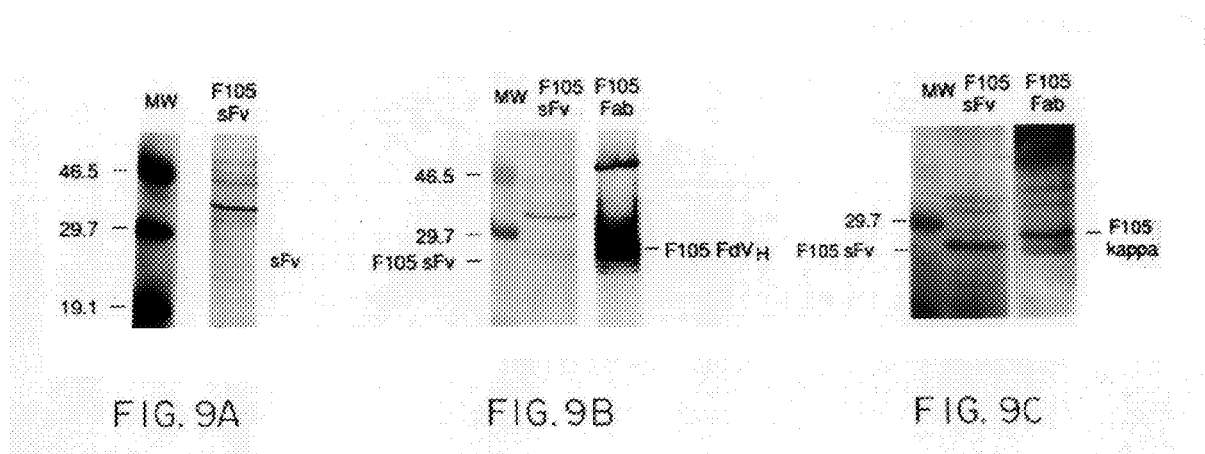

As shown in FIG. 9, expression of F105 sFv antibody fragment (rF105 sFv) in BL21(DE3) is readily documented following IPTG induction, both by Coomassie Blue staining of SDS-acrylamide gels (FIG. 9A) and on Western blots (FIG. 9B and FIG. 9C). The plasmid pETpelB (containing F105 sFv genes) was transformed into BL21(DE3) and cultivated under appropriate conditions at 37° C. After reaching O.D.$_{600}$ of 0.6 the cells were induced with 1 mM IPTG (control-no IPTG). Bacteria were harvested after a 2-hour incubation at 37° C. For protein detection, total cell lysates were separated on a 12.5% SDS-polyacrylamide gel. Coomassie Blue staining of the total cell extract show the appearance of strong protein bands at 28 kD which corresponds to the rF105 sFv protein. For Western blots, either rabbit anti-$V_H$4-FR1 or goat anti-human κ antisera were used as a primary antibody and were followed by immuno-detection using alkaline phosphatase as enzyme (FIG. 9C).

Figure 10:
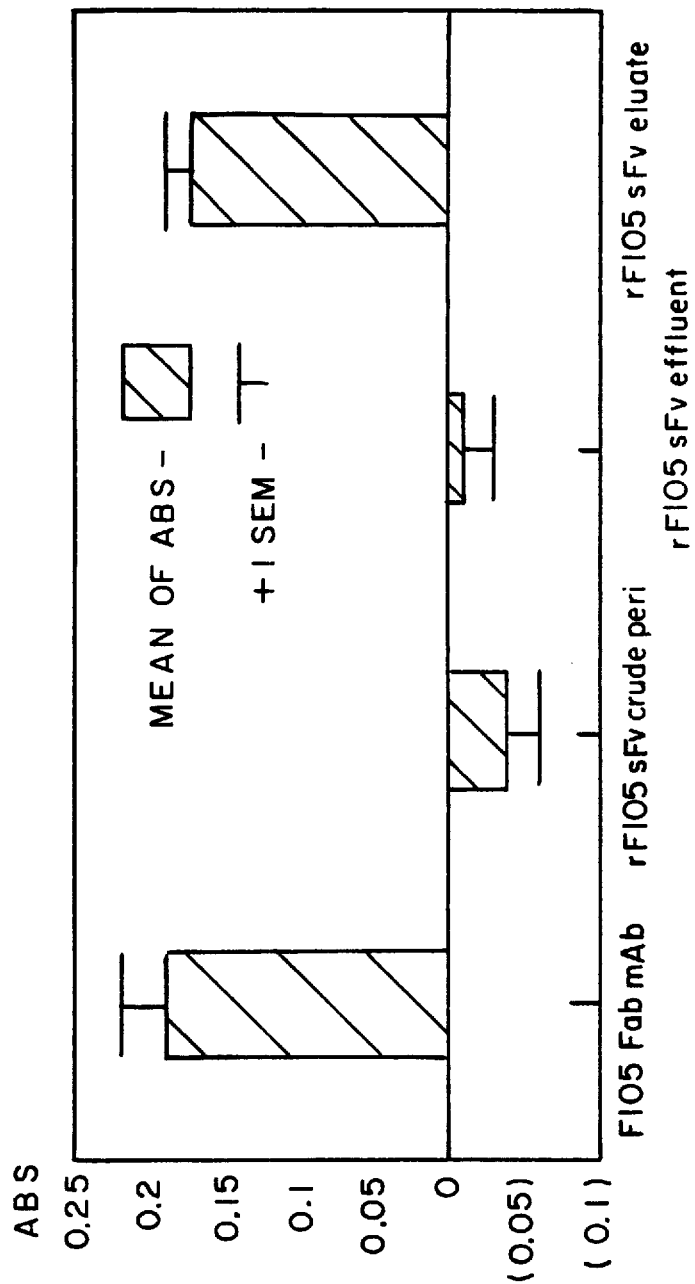

FIG. 10 shows the results of affinity column purification of rF105 sFv antibody fragments. Periplasm preparation of BL21(DE3) transformed with pETpelB vector containing the F105 sFv cassette were passed through a gp120 affinity column. Bound rF105 sFv was eluted with glycine-HCL (pH 2.6) followed by neutralization with 1M Tris-HCL (pH8.0). The pooled fractions were then analyzed by ELISA on gp120 coated plates. As can be seen in FIG. 10, gp120 affinity column purification of crude periplasm fractions resulted in the elution of gp120 binding activity whereas the effluent was devoid of binding activity.

TABLE 1

Reverse J$_H$ primers with 45 bp overlapping interchain linker:

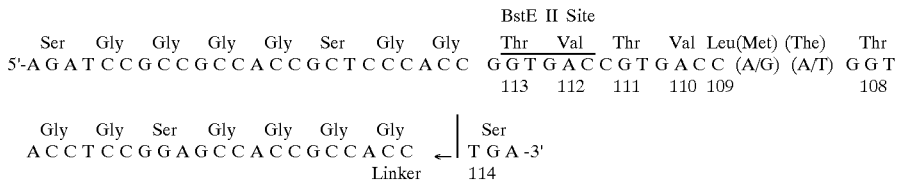

Forward human V$_K$ primer with 45 bp overlapping interchain linker:

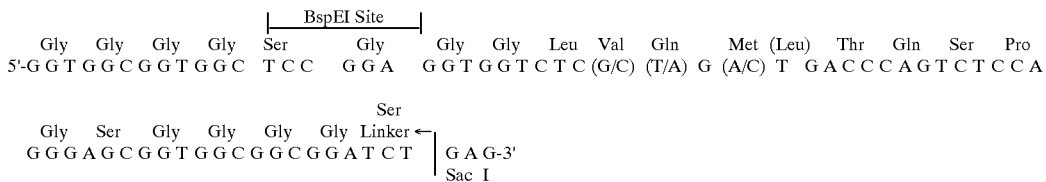

EXAMPLE IV
Expression of Hierarchical and Random Combinatorial Single Chain Antibodies as Phaae Antibodies The identification of sFvs that exhibit high affinity for gp120 is highly desirable for many reasons including understanding the serologic (gp120 epitope and antibody affinity) and molecular (selection of antibody genes used, generation of diversity through somatic mutations) nature of the patients' antibody response, for providing critical reagents for investigating the generation of such reactivities in viva and for therapeutic purposes. To generate the filamentous phage suitable of expressing the sFv antibody fragment as a fusion protein with the gene III protein, the fd phage previously used to generate phage antibodies by McCafferty, et al. [supra] is utilized. The human sFv gene is introduced into the identical position of the fd gene III as was successfully used by McCafferty, et al. First, single stranded phage DNA are prepared following transfection of the fd-tet vector (American Type Culture Collection) into F'dut-ung$E.$ coli (e.g., CJ236, RZ1032). rn vitro mutagenesis is employed to produce unique Kpn I and Eag I sites at positions 1611 and 1631 (see FIG. 13). These changes do not affect the coding sequence of gene III. A synthetic oligonucleotide is cloned into the Kpn I/Eag I-digested fed-tet DNA to reconstitute the deleted pIII coding sequence and to insert in-frame segments of the sFv gene. These flanking segments of the sFv gene contain the Xho I and Pvu II sites within the sFv gene that allow for cloning the full sFv cassette. The result is the fd-tet sFv vector, which encodes a pIII-sFv fusion protein, containing (from amino terminus to carboxy terminus) the pIII protein signal sequence (including the Ser-Ala-Glu signal peptidase cleavage site), the sFv, and the remaining pIII sequences.

Characterization of gp120 Reactive Phage Antibodies

Phage are generated by transfection of fd-tet-sFv vector into E. coli TG1 and are subsequently propagated in these bacteria while maintaining tetracycline selection. Control phage are generated by transfection of the fd-tet plasmid. High titer phage supernatants are polyethylene glycol precipitated and resuspended in approximately 1/100 of the original volume, followed by clearing residual bacteria and aggregated phage by centrifugation. The ability of the sFv-phage and control phage to bind gp120 is tested by ELISA, using a concentrated phage stock, as described by McCafferty, et al., [supra]. Briefly, gp120-coated plates are incubated with approximately $2 \times 10^{10}$ phage in phosphate-buffered saline containing 2% skimmed milk powder. Plates are washed with 0.5% Tween 20 in PBS followed by PBS, and bound phage are detected by sheep anti-M13 antisera (Sigma). Bovine serum albumin-coated plates are used as controls to ascertain if any reactivity seen is specific for gp120. The F105 human anti-gp120 sFv to determine the conditions to bind, elute and enrich for this F105 expressing phage. Typically each round of affinity purification results in a 1000-fold enrichment of high affinity clones. Phage in the eluate from the second round (or if necessary a third round) of affinity purification are cloned, propagated and their DNAs sequenced.

Similar experiments are performed using the repertoire libraries. See Example V. Analysis is performed on one patient at a time. Using the methodology discussed above, clones are selected which bind gp120 with high affinity. Each clone is DNA sequenced to ensure that they are not redundant clones. For further functional analysis of the anti-gp120 sFvs which are selected, the sFv cassette is removed from the fd-tet vector and cloned into the pET expression vector. These vectors are separately transformed into BL21(DE3) bacteria and, following concentration using an Amicon stir cell with a 10 kO cut off, these partially purified antibody fractions are assayed for different activities discussed below or further purified using a gp120 affinity column.

Virus neutralization with these anti-gp120 sFv antibodies are measured. Concentrated periplasm fractions or overnight culture supernatants (with appropriate negative controls) or affinity column purified sFvs are passed through a 0.45 μm filter and assayed as in specific aim 1 for virus neutralization. The sFv antibody affinity for gp120 is measured using a radioimmunoassay with $^{125}$I-gp120 and precipitating the sFV/gp120 complex with a rabbit anti-(ICL)interchain linker (Gly-Gly-Gly-Gly-Ser)$_3$ (SEQ ID NO:5) antisera which is prepared commercially. Additional epitope mapping is performed on the sFv antibodies which are recovered. PND ELISAs and F105 competition studies as discussed above is performed to epitope map their binding on gp120. Antibodies which appear to recognize a conformational determinant on gp120 are additionally analyzed for their ability to block gp120/sCD4 binding. For these studies, recombinant soluble CD4 (sCD4) is obtained from American Biotechnology, Inc. and is used to coat ELISA plates. HRP labeled gp120 is used to determine if these sFv antibodies can block HRP-gp120 binding as assayed by loss of HRP reactivity on the plates.

EXAMPLE V

REPERTOIRE CLONING OF REARRANGED HUMAN IMMUNOGLOBULIN GENES FROM PERIPHERAL BLOOD LEUKOCYTES (PBL)

Characterization of the Anti-gp120 Antibodies in HIV-1 Infected Patients

To produce hierarchical and random combinatorial libraries of rearranged immunoglobulin genes from the peripheral blood lymphocytes healthy HIV infected patients are reflected. The criteria for selection of these patients is based on their serologic reactivity (i.e., neutralization activity, F105 epitope blocking, V3 loop reactivity) and overall clinical status. Serum from healthy HIV infected patients are tested in an ELISA assay on EIA plates coated with recombinant gp120$_{MN}$ at 5–10 µg/ml or with individual V3 loop peptides at 2–5 µg/ml and blocked with 0.5% BSA. Thirteen amino acid peptides corresponding to the PND V3 loops (positions 307–319) of various strains of HIV are obtained from American Biotechnology Inc., Cambridge, Mass. Patients' sera is screened against several PNDs including IIIB, MN, SF2, RF and CC. After a 2-hour incubation at 37° C. and washing, plates are incubated with HRP coupled goat-anti-human IgG and color developed using azinobis (3-ethyl benzthiazoline sulfonic acid) containing 0.03% $H_2O_2$. Optical density is read at 410 nm using a Multiscan plate reader (Dynatech). These studies determine both the V3 loop reactivity and the total antibody titer to gp120.

The presence of antibodies which react with the broadly neutralizing, conformational determinant on gp120 which is recognized by F105 (Posner, et al., supra; Thali, et al., supra] is studied. For these studies, ELISA plates are coated with optimal concentrations of gp120$_{MN}$ which allow F105 binding. Various dilutions of patients' sera are tested for competition with biotinylated F105. Competition is documented by loss of avidin-HRP reactivity. To ensure that competition is not secondary to anti-id reactivity directly to F105 (and thus blocking F105 binding directly), protein A coated ELISA plates are incubated with patients' sera, washed, blocked by addition of normal human sera, washed again and then followed by addition of biotinylated F105 which has been mixed with normal human sera. Any avidin-HRP reactivity detected is secondary to anti-id reactivity to F105.

The ability of sera to neutralize diverse laboratory strains can be tested in two different assays:

1. by using production of reverse transcriptase activity by HT-H9 cells in a 7-day assay; and
2. by means of an MT-2 cell neutralization assay [Posner, et al., supra; Pawells, et al., *J. Virol. Methods*, 20:309 (1988); Mosmann, et al., *J. Immunol. Methods*, 65:55 (1983)]. Briefly, for the reverse transcriptase assays, various dilutions of patients' sera (or control sera) are incubated with 100 5% TCID of HIV$_{IIIB}$ or MN stock virus followed by incubation of HT-H9 cells with the antibody and virus mixture. Infected cells are then cultured for 7 days with a single feeding and supernatants assessed for reverse transcriptase activity (Posner, et al., supra]. The second neutralization assay is a slight modification of the MT-2 cell cytotoxicity assay [Pawels, et al., supra; Mosmann, et al., supra]. Serial dilutions of patients' sera are prepared in 50 ul complete medium in wells and 50 ul of appropriately diluted viral stock are added to each well. After 1 hour at 4° C., 100 ul of medium with 4×10$_4$ MT-2 cells is added. The plates are incubated for 5 days, then viable cells measured colorimetrically using metabolic conversion of the formazan dye MTT (Rossi, et al., *PNAS*, 86[8055–8059 (1990)]. Twenty microliters of MTT (5 mg/ml in PBS) is added to each well. After a 4-hour incubation, 100 ul of supernatant is removed and 130 ul of 10% TRITON X-100 in acid isopropanol is added and the samples pipetted to dissolve the precipitate. The optical density of the wells is determined at 540 nm, with a background subtraction at 690 nm. Per cent inhibition is calculated by the formula:

1-{(virus control- experimental)/(virus control-medium control)}.

The MT-2 assay is less labor intensive than the RT assay and suited to larger experiments and will be the major assay used in these screening studies.

For repertoire cloning, each patient is subjected to phlebotomy with the intent of obtaining approximately 1–3×10$^8$ lymphocytes (circa 250 ml) [Persson, et al., *PNAS*, 88:2432–2436 (1991)]. The leukocyte fraction is further purified by density-gradient separation (Ficoll-Hypaque; Pharmacia). It is anticipated that 1×10$^6$ lymphocytes/ml processed blood by this method of which approximately 10% are B cells. RNA is isolated immediately by guanidinium isothiocyante method [Chomczynski, et al. *Analytical Biochemistry*, 162:156 (1987)]. After completion of isolation, RNA is stored precipitated by 50% isopropanol in 3M guanidinium isothiocyanate with 2-mercaptoethanol at −20° C. until used for reverse transcription.

Figure 7:
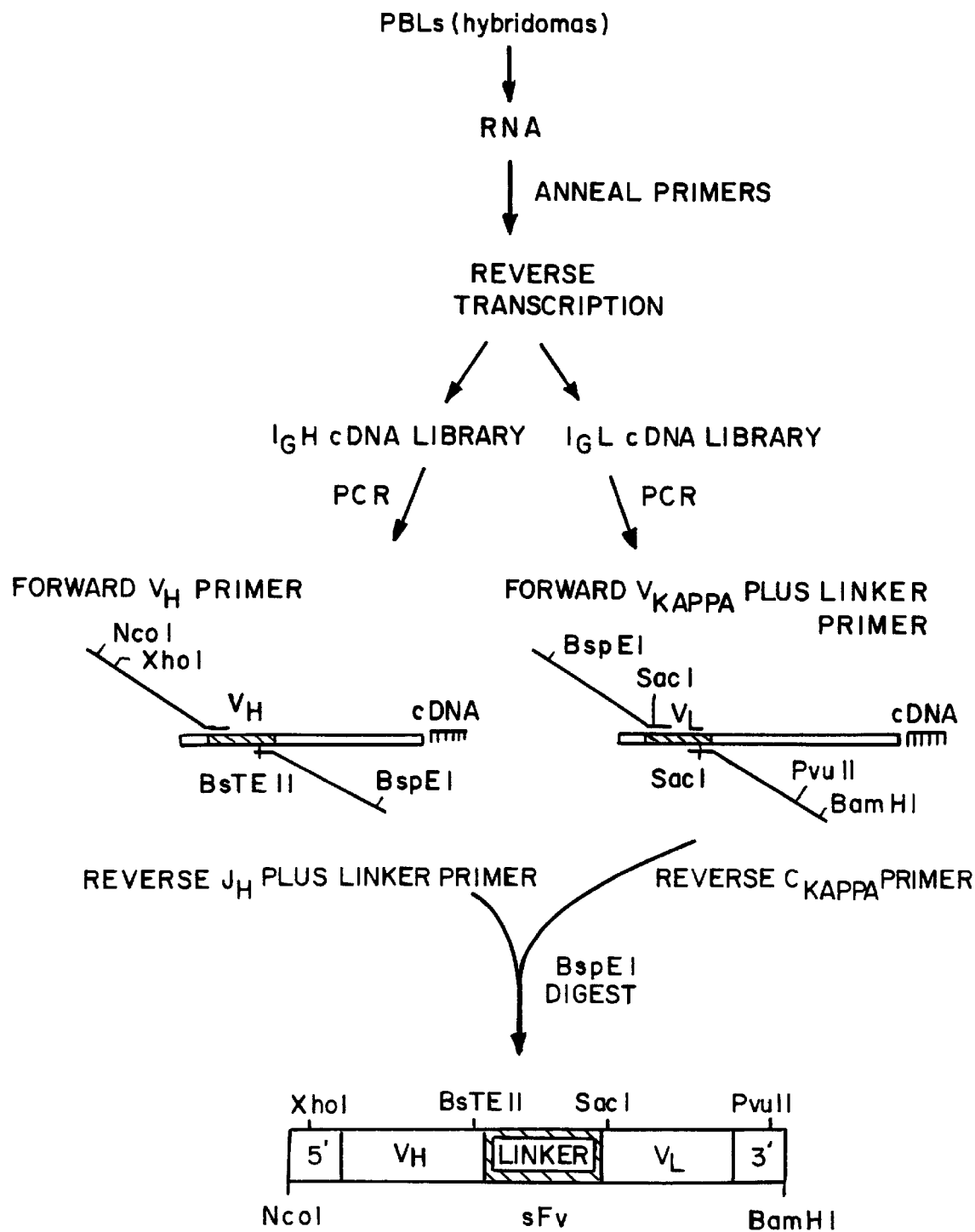

For the immunoglobulin gene library construction (FIG. 7), total RNA (20–50 µg) is added to 60 pmol of either a γ 1, κ or λ genes. The reaction mixtures is subjected to 25–30 rounds of amplification. For hierarchical library formation, the V$_H$71-4 and Humvk325 leader sequence primers are used along with J$_H$ and J$_κ$ (or C$_κ$) primers respectively. See Example I for primer sequences. Following an initial 20–25 rounds of amplification, the PCR product is gel purified and re-amplified with the degenerate V$_H$ and V$_κ$ primers. This allows a restricted sFv library to be created for cloning into the phage antibody vector. For the random combinatorial library, the degenerate V$_H$ and V$_κ$ primers are used initially.

EXAMPLE VI

CHARACTERIZATION OF THE REARRANGED F105 V$_H$ GENE

DNA sequence analysis revealed that the rearranged F105 V$_H$ gene is derived from a member of the V$_H$IV gene family as determined by the greater than 88% similarity with all of the identified members of the germ line V$_H$ genes that have recently been identified by Lee, et al., [Lee, et al., *J. Mol. Bio.*, 195:761–768 (1987)] (data not shown). This newly discovered V$_H$ gene family has approximately 10 members. F105 V$_H$ shares greatest sequence similarity with germ line gene V$_H$71-4 (94.8%, 285/297 nucleotides) (Table 2). There are a total of twelve nucleotide changes in F105 compared to 71-4 and these changes are summarized in Table 2. Nine of the changes are in the framework residues which are distributed in all three framework residues which are distributed in all three framework regions. These changes include four transitions and five transversions. The remaining three changes are all transitions and occur in the CDR1

(one) and CDR2 (two) regions. Table 2 also compares the nucleotide sequence of F105 $V_H$ to three additional non-rearranged $V_H$ IV germline genes ($V_H$ 4.11, 4.15 and 4.16) that were identified by PCR amplification of genomic DNA from an adult healthy Caucasian donor. These three germline genes are most closely related to $V_H$ 71-4 [Sanz, et al., *EMBO J.*, 8:3741–3748 (1989)]. As can be seen, all three of these germline genes and F105 share the G-A nucleotide; Val→Ile amino acid change in position 29 supporting the possibility that this change may represent an allelic polymorphism. F105, however, has many more nucleotide changes [Goudsmit, et al, *PNAS*, supra] compared to these genes (one, 4.11: or two, 4.15 and 4.16) suggesting that additional somatic mutations might have arisen in F105 after recombination.

TABLE 2

NUCLEOTIDE SEQUENCE COMPARISON OF F105 $V_H$
AND SEVERAL SIMILAR GERMLINE $V_H$IV GENES

```
                  -19                                                      -10
V_H71-4:   ATG  AAA  CAT  CTG  TGG  TTC  TTC  CTT  CTC  CTG  GTG  GCA  GCT  CCC  AGA  T/GG
F105V_H:   ...  G..  ...  ...  ...  ...  ...  ...  ...  ...  ...  ...  ...  ...  ...  ...

VH411:     ...  ...  ...  ...  ...  ...  ...  ...  ...  ...  ...  ...  ...  ...  ...  ...

VH415:     ...  ...  ...  ...  ...  ...  ...  ...  ...  ...  ...  ...  ...  ...  ...  ...

VH416:     ...  ...  ...  ...  ...  ...  ...  ...  ...  ...  ...  ...  ...  ...  ...  ...

1                                                       10
V_H71-4:   GTC  CTG  TCC  CAG  GTG  CAG  CTG  CAG  GAG  TCG  GGC  CCA  GGA  CTG  GTG  AGG
F105V_H:   ...  ...  ...  ...  ...  ...  ...  ...  ...  ...  ...  ...  ...  ...  ...  ...

VH411:     ...  ...  ...  ...  ...  ...  ...  ...  ...  ...  ...  ...  ...  ...  ...  ...

VH415:     ...  ...  ...  ...  ...  ...  ...  ...  ...  ...  ...  ...  ...  ...  ...  ...

VH416:     ...  ...  ...  ...  ...  ...  ...  ...  ...  ...  ...  ...  ...  ...  ...  ...

20
V_H71-4:   CCT  TCG  GAG  ACC  CTG  TCC  CTC  ACC  TGC  ACT  GTC  TCT  GGT  GGC  TCC  GTC
F105V_H:   ...  ...  ...  ...  ...  ...  ...  ...  ...  ...  ..A  ...  ...  ...  A..  ...

VH411:     ...  ...  ...  ...  ...  ...  ...  ...  ...  ...  ...  ...  ...  ...  A..  ...

VH415:     ...  ...  ...  ...  ...  ...  ...  ...  ...  ...  ...  ...  ...  ...  A..  ...

VH416:     ...  ...  ...  ..C  ...  ...  ...  ...  ...  ...  ...  ...  ...  ...  A..  ...

30                      CDR1                                   40
V_H71-4:   AGT  ***  ***  AGT  ***  TAC  TAC  TGG  AGC  TGG  ATC  CGG  CAG  CCC  CCA  GGG
F105V_H:   ...  ...  ...  ...  ...  ..C  ...  ...  ...  ...  ...  ...  ...  ..T  ...  ...

VH411:     ...  ...  ...  ...  ...  ...  ...  ...  ...  ...  ...  ...  ...  ...  ...  ...

VH415:     ...  ...  ...  ...  ...  ...  ...  ...  ...  ...  ...  ...  ...  ...  ...  ...

VH416:     ...  ...  ...  ...  ...  ...  ...  ...  ...  ...  ...  ...  ...  ...  ...  ...

50              CDR2            60
V_H71-4:   AAG  GGA  CTG  GAG  TGG  ATT  GGG  TAT  ATC  TAT  TAC  AGT  GGG  AGC  ACC  AAC
F105V_H:   ...  ...  ...  ..C  ...  ...  ...  ..A  ...  ...  ..C  ...  ...  ...  ...  ...

VH411:     ...  ...  ...  ...  ...  ...  ...  ...  ...  ...  ...  ...  ...  ...  ...  ...

VH415:     ...  ...  G..  ...  ...  ...  ...  ...  ...  ...  ...  ...  ...  ...  ...  ...

VH416:     ...  ...  ...  ...  ...  ...  ...  ...  ...  ...  ...  ...  ...  ...  ...  ...

70
V_H71-4:   TAC  AAC  CCC  TCC  CTC  AAG  AGT  CGA  GTC  ACC  ATA  TCA  GTA  GAC  ACG  TCC
F105V_H:   ...  .G.  ...  ...  ...  ...  ...  ...  ...  ...  ...  ...  ..G  ...  ...  ...

VH411:     ...  ...  ...  ...  ...  ...  ...  ...  ...  ...  ...  ...  ...  ...  ...  ...

VH415:     ...  ...  ...  ...  ...  ...  ...  ...  ...  ...  ...  ...  ...  ...  ...  ...

VH416:     ...  ...  ...  ...  ...  ...  ...  ...  ...  ...  ...  ...  ...  ...  ...  ...
```

TABLE 2-continued

NUCLEOTIDE SEQUENCE COMPARISON OF F105 $V_H$ AND SEVERAL SIMILAR GERMLINE $V_H$IV GENES

```
                                  80
V_H71-4:  AAG AAC CAG TTC TCC CTG AAG CTG AGC TCT GTG ACC GCT GCG GAC ACG
F105V_H:  ... ... ... ... ... ... ... ... .C. ... A.. ... ... ... ... ...

VH411:    ... ... ... ... ... ... ... ... ... ... ... ... ... ... ... ...

VH415:    ... ... ... ... ... ... ... ... ... ... ... ... ... ... ... ...

VH416:    ... ... ... ... ... ... ... ... ... ... ... ... ... ... ... ...

90
V_H71-4:  GCC GTG TAT TAC TGT GCG AGA
F105V_H:  ... ... ... ... ... C.. ...

VH411:    ... ... ... ... ... ... ...

VH415:    ... ... ... ... ... ... ...

VH416:    ... ... ... ... ... ... ...
```

At the amino acid level, four of the F105 $V_H$ nucleotide changes result in the silent mutations which are distributed equally in each of the three framework regions (positions 26, FR1; 49, FR2; 94, FR3) and there is one silent mutation in CDR2 (position 52). The remaining eight nucleotide changes result in amino acid changes which occur in the three framework regions more frequently than in the CDRs (Table 3). Two non-conservative changes occur in the FR2 region (positions 40, Pro→Ser; 46, Glu→Gln) and three conservative changes occur in the FR3 region (positions 72, Asp→Glu; 82A, Ser→Thr; 82C, Val→Met). One additional FR1 region framework residue at position 29, which results in a conservative change Val→Ile, is located immediately adjacent to the CDR defined by Kabat, et al. [Kabat, et al., supra]. This region may also contribute to the topography of the antibody combining site [Clothia, et al., *J. Mol. Bio.*, 196:901–907 (1987)]. The presence of Ile at position 29 in four of seven germ line $V_H$ IV genes (all G→A nucleotide changes) suggests that Ile may represent an allelic difference and not a somatic mutation [Lee, et al., supra; Sanz, et al., supra]. In the CDR regions, two changes occur with a non-conservative replacement of Tyr→His in CDR1, position 32 and a semi-conservative change of Asn→Ser in CD2, position 60. Overall, the ratio of substitution to silent mutations is 2:1. The substitution mutations occur in a FR/CDR ratio of 3:1.

Comparative Analysis of F105 $V_H$ and Other $V_H$ 71-4 Derived Rearranged $V_H$ Genes Table 4, panel A compares the nucleotide sequence of F105 $V_H$ to two monoclonal antibodies, which by nucleotide sequence analysis, appear to use a rearranged $V_H$ 71-4 gene. One IgM monoclonal antibody (Ab26) was derived from CD5+ B cells of a healthy donor and represents a naturally occurring polyreactive

TABLE 3

A. SUMMARY OF DIFFERENCES BETWEEN F105 $V_H$ AND GERM LINE 11-4 $V_H$

| | | Nucleotide | | | Amino Acid | | |
|---|---|---|---|---|---|---|---|
| Pos. | Location | 71-4 | F105 | Change | 71-4 | F105 | Change |
| 26 | FR1 | T | A | TV | Gly | Gly | Silent |
| 29 | FR1 | G | A | TS | Val | Ile | Conservative |
| 32 | CDR1 | T | C | TS | Tyr | His | Non-Conservative |
| 40 | FR2 | C | T | TS | Pro | Ser | Non-Conservative |
| 46 | FR2 | G | C | TV | Glu | Gln | Non-Conservative |
| 49 | FR2 | G | A | TS | Gly | Gly | Silent |
| 52 | CDR2 | T | C | TS | Tyr | Tyr | Silent |
| 60 | CDR2 | A | G | TS | Asn | Ser | Semi-Conservative |
| 72 | FR3 | C | G | TV | Asp | Glu | Conservative |
| 82A | FR3 | G | C | TV | Ser | Thr | Conservative |
| 82C | FR3 | G | A | TS | Val | Met | Conservative |
| 94 | FR3 | A | C | TV | Arg | Arg | Silent |

TABLE 3-continued

B. SUMMARY OF DIFFERENCES BETWEEN F105 V$_k$
AND GERM LINE Humvk325

| | | Nucleotide | | | | Amino Acid | |
|---|---|---|---|---|---|---|---|
| Pos. | Location | vk325 | F105 | Change | vk325 | F105 | Change |
| 15 | FR1 | C | G | TV | Pro | Ala | Non-Conservative |
| 31 | CDR1 | C | G | TV | Ser | Arg | Non-Conservative |
| 78 | FR3 | C | G | TV | Leu | Val | Conservative |
| 90 | CDR3 | G | A | TS | Glu | Glu | Silent |
| 92 | CDR3 | G | A | TS | Gly | Asp | Non-Conservative |
| 94 | CDR3 | G | A | TS | Ser | Asn | Non-Conservative |
| 95A | CDR3 | C | G | TV | Pro | Val | Non-Conservative |
| 95B | CDR3 | C | T | TS | Pro | Val | Non-Conservative |

TS = Transition;
TV = Transversion

TABLE 4

A. NUCLEOTIDE SEQUENCE COMPARISON OF F105 V$_H$ TO SOMATIC REARRANGED V$_H$ 71-4 GENES

```
          -19                                                    -10
V_H71-4: ATG AAA CAT CTG TGG TTC TTC CTT CTC CTG GTG GCA GCT CCC AGA T/GG
F105V_H: ... G.. ... ... ... ... ... ... ... ... ... ... ... ... ... ...

Ab26:    ... ... ... ... ... ... ... ... ... ... ... ... ... ... ... ...

268-D:   ... ... ... ... ... ... ... ... ... ... ... ... ... ... ... ...

1                                       10
V_H71-4: GTC CTG TCC CAG GTG CAG CTG CAG GAG TCG GGC CCA GGA CTG GTG AAG
F105V_H: ... ... ... ... ... ... ... ... ... ... ... ... ... ... ... ...

Ab26:    ... ... ... ... ... ... ... ... ... ... ... ... ... ... ... ...

268-D:   ... ... ... ... ... ... ... T.. ... . T. ... ... ... ... ... ...

20
V_H71-4: CCT TCG GAG ACC CTG TCC CTC ACC TGC ACT GTC TCT GGT GGC TCC GTC
F105V_H: ... ... ... ... ... ... ... ... ... ... ... ... ..A ... ... A..

Ab26:    ... ..A C.. ... ... ... ... ... ..T ... ... ... ... ... ... A..

268-D:   ... ... ... ... ... ... ... ... ... ... ... ... ... C.. A..

30                  CDR1                              40
V_H71-4: AGT *** *** AGT *** TAC TAC TGG AGC TGG ATC CGG CAG CCC CCA GGG
F105V_H: ... ... ... ... ... C.. ... ... ... ... ... ... ... T.. ... ...

Ab26:    ... ... ... ... GGT G. T ... ... ... ... ... ..C ... .A. ... ...

268-D:   .A. *** *** .A. *** GC. ... ... .CA ... ... ... .A ... ... ...

50              CDR2          60
V_H71-4: AAG GGA CTG GAG TGG ATT GGG TAT ATC TAT TAC AGT GGG AGC ACC AAC
F105V_H: ... ... ... C.. ... ... ..A ... ... ..C ... ... ... ... ... ...

Ab26:    ... ..C ... ... ... ... ... ..C ..A ... ... ... ... ... ... ...

268-D:   ... ..G ..A ... .AC C.. ..A ... G.. ... C.T .C. ..A GT. ... ...

70
V_H71-4: TAC AAC CCC TCC CTC AAG AGT CGA GTC ACC ATA TCA GTA GAC ACG TCC
F105V_H: ... .G. ... ... ... ... ... ... ... ... ... ... ... ..G ... ...

Ab26:    ... ... ... ... ... ... ... ... ..T G.. ... ... ..G ... ... ..T

268-D:   ... ..T ... ... ... ..C ..G C.. ... ... A.. A.. ... ... ...

80
V_H71-4: AAG AAC CAG TTC TCC CTG AAG CTG AGC TCT GTG ACC GCT GCG GAC ACG
F105V_H: ... ... ... ... ... ... ... ... .C. ... A.. ... ... ... ... ...
```

TABLE 4-continued

```
Ab26:   ...  ... ... ...  ...  ...  ...  ...  ...  ...  ...  ...   ...   ...  ...
268-D: . G.  ... G ... ... A ...  ... C . GC ... . AG . T. ... ... ... ... ... ... T. .

90
V_H71-4: GCC GTG TAT TAC TGT GCG AGA
F105V_H: ...  ...  ...  ...  ...  ...  C. .

Ab26:    ...  ...  ...  ...  ...  ...  . C.

268-D:   ...  . . A ...  ... T ...  ...  ...
```

B. AMINO ACID SEQUENCE COMPARISON OF F105 V_H TO SOMATIC REARRANGED V_H71-4 GENES

```
         -19                                      1                    10
V_H71-4: M K H L W F F L L L V A A P R W V L S Q V Q L Q E S G P G L V
F105V_H: . E . . . . . . . . . . . . . . . . . . . . . . . . . . . . .

Ab26:    . . . . . . . . . . . . . . . . . . . . . . . . . . . . . . .

268-D:   . . . . . . . . . . . . . . . . . . . . . V . . . . . . . . .

20                          30        CDR1
V_H71-4: K P S E T L S L T C T V S G G S V S * * S * Y Y W S W I R Q
F105V_H: . . . . . . . . . . . . . . . . . I . * * . * H . . . . . . .

Ab26:    . . . Q . . . . . . . . . . . . . I . . . . G D . . . . . . .

268-D:   . . . . . . . . . . . . . . . . P I N * * N * A . . T . . . .

40                    50         CDR2   60                       70
V_H71-4: P P G K G L E W I G Y I Y Y S G S T N Y N P S L K S R V T I S
F105V_H: S . . . . . Q . . . . . . . . . . . . . . S . . . . . . . . .

Ab26:    H . . . . . . . . . . . . . . . . . . Y . . . . . . . A . . .

268-D:   . . . . . . . . Y L . . V . H T . V . . . . . . . . . L . . T 80                          90
V_H71-4: V D T S K N Q F S L K L S S V T A A D T A V Y Y C A R
F105V_H: . E . . . . . . . . . . . T . M . . . . . . . . . . .

Ab26:    . . . . N . . . . . N . N . . . . . . . . . . . . S .

268-D:   I . . . R K . L . . S . K F . . . . . S . . . . . . .
``` antibody which binds to many antigens [Sanz, et al., *J. Immunol.*, 142:4054–4061 (1989)]. Ab26 has greatest sequence similarity with V_H71-4 (92.3%) compared to the next closest germline gene V_H71-2 (89.5%). Also shown in Table 3 is antibody 268–0, an IG_1 mAb which is specific for the principle neutralizing domain of gp120 of HIV-1 strain MN and is 88.5% identical to V_H71-4 [Andris, et al., *PNAS*, 88:7783–7787 (1991)]. As can be seen in Table 4, all three of these V_H71-4 related heavy chains have undergone extensive somatic mutation with F105 showing the least number of nucleotide changes. For monoclonal antibodies Ab26 and 268-D, there are 19 and 42 nucleotide changes, respectively. In all of these examples, nucleotide changes are scattered in both the CDR and FR regions. All three antibodies have the G→A nucleotide change in amino acid position 29 as does F105. Table 4, lower panel shows the corresponding amino acid changes in these three monoclonal antibodies. For antibodies Ab26 and 268-D, there are 11 and 23 amino acid changes respectively compared with F105 which has 8 changes. The only change shared by three antibodies is Val→Ile in position 29.

Analysis of the F105 D_H Gene Encoding CDR III

The D_H portion in V_H-D_H-J_H structure corresponds to the complementarity determining region (CDR) III of H chain [Schilling, et al., *Nature*, 283:35–40 (1980)]. Over twenty human germ line genes have been identified and it is estimated that the total number of D_H genes is approximately thirty [Ichihara, et al., *EMBO J.*, 7:4141–4150 (1988)]. As shown in Table 5 (panel A), the F105 D_H region appears to be composed of a D—D fusion product [Meek, et al., *J. Exp. Med.*, 170:39–57 (1989); Eilat, et al., supra; Yamada, et al., *J. Exp. Med.*, 173:395–407 (1991); Sanz, et al., *J. Immunol.*, supra]. A seven nucleotide sequence in the center of the F105 D_H gene is identical to the germ line D_H gene dlr4. This region of identity is immediately flanked on its 5' end by an additional ⅔ identical nucleotides compared to dlr4. The additional 5' nucleotides found in F105 D_H which are rich in dG and dCs probably represent random "N segment" nucleotide additions since these are the favored nucleotides of the enzyme terminal deoxynucleotidyltransferase (Tdt) [Kipps, et al., *J. Clin. Invest.*, 87:2087–2096 (1991)]. Examination of 3' end of the F105 D_H region shows that 11/13 nucleotides are identical to the da4/da1 germ line gene. The 3' end of this nucleotide sequence may extend into the 5' end of the J_H region, the precise boundary of which is difficult to define accurately because of this identify with the da4/da1 germline D_H gene. Since both of these D_H genes are in the same transcriptional orientation, rearrangement probably occurred by deletion rather than by inversion [Meek, et al., supra).

A GeneBank search for other rearranged human heavy chain genes which that have nucleotide sequence homologies with the F105 $D_H$ gene revealed two rearranged genes (L17 and L37). These have a relatively short $D_H$ segment (approximately 24 nucleotides) compared to F105 but contain near their 5' end the same 12 nucleotide "core" that is identical to 12 nucleotides at the 3' end of the F105 $D_H$ gene (Table 4, panel 8) [Alt, et al., *PNAS*, 79:4118–4122 (1982)]. This observation is in agreement with other studies which show that all three coding frames appear to be used equally in the human [Ichihara, et al, supra; Yamada, et al., supra] although preferential use of one reading frame has been demonstrated with anti-DNA antibodies [Dersimonian, et al., *J. Immunol.*, 142:4027–4033 (1989)] and with certain germline $D_H$ genes [Yamada, et al., supra].

TABLE 5

A. COMPARISON OF F105 $D_H$ GENE WITH HUMAN GERMLINE $D_H$ REGION GENES

| | | |
|---|---|---|
| dlr4 | AGGATATTGTAGTAGTACCAGCTG | CTATGCC |
| F105 | Ggccc c GTgCCAGCTGt c t t CTAc Ggt gactac | |
| F105 | ggccccgt gccagct gt ct t CTACg GTg ACTAC | |
| da4 | | TGACTACAGTAACTAC |
| da1 | | TGACTACAGTAACTAC |

Nucleotide sequences of 3 human germline $D_H$ genes dlr4, da4 and da1 [Eilat, et al., J. Immunol. 147:361-368 (1991)]. Underlined nucleotides show identity between F105 D region and a known germline $D_H$ gene.

B. COMPARISON OF THE F105 AND L17/L37 $D_H/J_H$ BOUNDARIES

| Kabat Position- | 95 | 96 | 97 | 98 | 99 | 100 | A | B | C | D | E | | |
|---|---|---|---|---|---|---|---|---|---|---|---|---|---|
| F105 Amino Acid | Gly | Pro | Val | Pro | Ala | Val | Phe | Tyr | Gly | Asp | Tyr | | |
| F105 Nucleotide | GGC | CCC | GTG | CCA | GCT | GTC | TTC | TAC | GGT | GAC | TAC | | |
| L17/L37 Nucleotide | | | | | | ggg | agT | ACG | GTG | ACT | ACg | gga | gat |
| L17/L37 Amino Acid | | | | | | Gly | Ser | Thr | Val | Thr | Thr | Gly | Asp |
| Kabat Position- | | | | | | 96 | 97 | 98 | 99 | 100 | A | B | C |

L17/L37 are rearranged $D_H$ region genes which are derived from tonsillar lymphocytes that express the $V_HI$ related G6 cross-reactive idiotype [Silverman, et al., *Arthritis Rheum.*, supra]. Underlined nucleotides show identity between F105 D region and the L17/L37 D region genes.

L17/L37 are rearranged $D_H$ region genes which are derived from tonsillar lymphocytes that express the $V_H1$ related G6 cross-reactive idiotype [Silverman, et al., *Arthritis Rheum.*, supra]. Underlined nucleotides show identity between F105 D region and the L17/L37 D region genes.

Analysis of the F105$J_H$ Region Gene

Comparison of the F105 $J_H$ region with the six human $J_H$ germ line genes reveals greatest sequence similarity with $J_{H5}$ (Table 6). The F105 $J_H$ region differs by six nucleotides from that of $J_{H5}$. Five of these differences are clustered at the 5' end of the $J_H$ gene. These five differences result in four amino acid changes. Non-conservative changes occur at position 100E, Asn→Tyr; 100F, Trp→Arg; 101, Phe→Leu and 103, Ser→Pro. The sixth nucleotide change, in amino acid position 106 which lies outside of CDR3, is silent. It is possible that the amino acid corresponding to position 100E in $J_{H5}$ is deleted in F105 $J_H$.

F105 Heavy Chain Shares in CDR2 Idiotope HV2a

Silverman, et al., [Silverman, et al., *Eur. J. Immunol.*, supra] used peptide antisera raised against consensus peptides from the first framework (FR1) and second CDR region (CDR2) of human $V_H$ IV heavy chains to make heavy chain class assignments for cold aggulutinin and rheumatioid factor antibodies [Silverman, et al., *Eur. J. Immunol.*, supra; Silverman, et al, *Arthritis Rheum.* supra]. The CDR2 consensus peptide HV2a for these antibodies could not distinguish among three different $V_HIV$ germline genes (V71-2, V71-4 and V79) [Silverman, et al., *Eur. J. Immunol.*, supra]. The results demonstrated that both cold agglutinin and a subgroup of rheumatoid factor heavy chains both reacted with FR1 antibodies but only cold agglutinin antibodies reacted with anti-$V_H4$-HV2a antisera. In Western blot experiments with F105. As can be seen, anti-$V_H4$-FR1 antisera reacts with F105, whereas anti-$V_H3$-FR1 antisera does not react with F105. F105 also reacts with anti-$V_H4$-HV2a and this binding is markedly inhibited by preincubation of anti-$V_H4$-HV2a with $V_H4$-HV2a peptide, but not with the closely related $V_H4$-2c peptide.

TABLE 6

COMPARISON OF F105 $J_H$ TO GERMLINE $J_{H5}$

| $J_{H5}$ | Asn | –Trp | –Phe | –Asp | –Ser | –Trp | –Gly | –Glu | –Gly | –Thr | –Pro | –Val | –Thr | –Val | –Ser | –Ser |
|---|---|---|---|---|---|---|---|---|---|---|---|---|---|---|---|---|
| $J_{H5}$ | AAC– | TGG– | TTC– | GAC– | TCC– | TGG– | GGC– | CAA– | GGA– | ACC– | CTG– | GTC– | ACC– | GTC– | TCC– | TCA |
| F105 | T**– | C*A– | C– | – | C– | **– | – | G– | *– | *– | *– | *– | *– | *– | *– | * |
| F105 | Tyr | –Arg | –Leu | –*– | Pro | –*– | **– | Glu | –*– | *– | *– | *– | *– | *– | *– | *** |

POS.  100E 100F 101–102–103–104–105–106–107–108–109–110–111–112–113–114

NOTE- Four somatic mutations which are clustered at the 5' end of F105 $J_H$ in positions 100E, 100F, 101 and 103 result in substitution mutations whereas the fifth somatic mutations in position 106 is silent.

NOTE-Four somatic mutations which are clustered at the 5' end of F105 $J_H$ in positions 100E, 100F, 101 and 103 result in substitution mutations whereas the fifth somatic mutations in position 106 is silent. This result indicates that the F105 $V_H$ is structurally more closely related to the cold agglutinin heavy chains than to the rheumatoid factor heavy chains.

F105 Light Chain $V_K$ Gene Is Derived From Germ Line Humvk325 Germ Line Gene

DNA sequence analysis revealed that the rearranged F105 $V_k$ gene is derived from a member of the $V_k$ III subgroup gene family [Kabat, et al., supra]. The $V_k$ III subgroup can be further subdivided into sub-subgroups, one of which is the $V_k$ IIIb sub-subgroup. F105 shares the greatest sequence similarity with the $V_k$ IIIb germline gene Humvk325 (97.7%, 343/351 nucleotides) (Table 7, Panel A). There are a total of eight nucleotide changes in F105 $V_k$ compared to Humvk325 and these changes are summarized in Table 3. Two of the changes, which are both transversions, are located in the framework regions FR1 and FR3. Six additional changes, including 4 transitions and 2 transversions, are located in CDR1 [Gallo, et al., supra] and CDR3 [Patterson, et al., J. Gen. Virol., 68:1177–1181 (1987)].

At the amino acid level, only one of the nucleotide changes results in a silent mutation. Of the remaining seven nucleotide changes, two changes occur in framework regions and five occur in the CDR regions (Table 3 and 7, panel 8). The two framework changes include a non-conservative change FR1 (position 15, Pro→Ala) and a conservative change in FR3 (position 78, Leu→Val). In the CDR regions, one change occurs with a non-conservative substitution of Ser→Arg in CDR1, position 31. There are three non-conservative amino acid changes in CDR3 including Gly→Asp, Ser→Asn, and Pro→Val in positions 94, 95A and 95B, respectively. The last amino acid change is the result of two individual point mutations that occur in a FR/CDR ratio of 1:2. This is in marked contrast to the pattern of changes observed for the F105 $V_H$ sequence (Table 3).

TABLE 7

A. NUCLEOTIDE SEQUENCE COMPARISON OF F105 $V_k$ WITH GERMLINE GENE Humvk325

```
              -20                                                  -10
   vk325:  ATC GAA ACC CCA GCG CAG CTT CTC TTC CTC CTG CTA CTC TGG CTC CCA
  F105Vk:  ... G.. ... ... ... ... ... ... ... ... ... ... ... ... ... ...

1                                    10
   vk325:  GAT ACC ACC GGA GAA ATT GTG TTG ACG CAG TCT CCA GGC ACC CTG TCT
  F105Vk:  ... ... ... ... ... ... ... ... ... ... ... ... ... ... ... ...

20                  CDR1
   vk325:  TTG TCT GCA GGG GAA AGA GCC ACC CTC TCC TGC AGG GCC AGT CAG AGT
  F015Vk:  ... ... C.. ... ... ... ... ... ... ... ... ... ... ... ... ...

30                                     40
   vk325:  GTT AGC AGC AGC TAC TTA GCC TGG TAC CAG CAG AAA CCT GGC CAG GCT
  F105Vk:  ... ... ... ... ..G ... ... ... ... ... ... ... ... ... ... ...

50            CDR2
   vk325:  CCC AGG CTC CTC ATC TAT GGT GCA TCC AGC AGG GCC ACT GGC ATC CCA
  F105Vk:  ... ... ... ... ... ... ... ... ... ... ... ... ... ... ... ...

60                                     70
   vk325:  GAC AGG TTC AGT GGC AGT GGG TCT GGG ACA GAC TTC ACT CTC ACC ATC
  F105Vk:  ... .G. ... ... ... ... ... ... ... ... ... ... ..G ... ... ...
```

TABLE 7-continued

```
                        80                                                      90
vk325:  AGC AGA GTG GAG CCT GAA GAT TTT GCA GTG TAT TAC TGT CAG CAA TAT
F105Vk: ... ... C.. ... ... ... ... ... ... ... ... ... ... ... ..G ...

CDR3
vk325:  GAT AAC TCC GTT TGC          Jk2:  TAC ACT TTT GGC CAG GGG ACC AAG

F105Vk: .G. .G. ..A CC. ...           F105: .GT ... ... ... ... ... ... ...

Jk2   : CTG GAG ATC AAA CGT

F105Jk: ... ... ... ... ..A
```

B. AMINO ACID SEQUENCE COMPARISON OF $F105_k$ WITH GERMLINE Humvk325 AND A RELATED REARRANGED k CHAIN

```
        -20                                           1                      10
vk325:  M E T P A Q L L F L L L L W L P D T T G E I V L T Q S P G T L
F105Vk: . . . . . . . . . . . . . . . . . . . . . . . . . . . . . .

neu:                                                    . . . . . . . . . .

20                CDR1    30                      40
vk325:  S L S P G E R A T L S C R A S Q S V S S S Y L A W Y Q Q K P G
F105Vk: . . . A . . . . . . . . . . . . . . . . . R . . . . . . . . .

neu:    . . . . . . . . . . . . . . . . . . . . . R . . . . . . . . .

50       CDR2              60                       70
vk325:  Q A P R L L I Y G A S S R A T G I P D R F S G S G S G T D F T
F105Vk: . . . . . . . . . . . . . . . . . . . . . . . . . . . . . .

neu:    . . . . . . . . . . . . . . . . . . . . . . . . . . . . . .

80                  90      CDR3
vk325:  L T I S R L E P E D F A V Y Y C Q Q Y G S S P
F105Vk: . . . . . V . . . . . . . . . . . . D N . V neu:    . . V . . . . . . . . . . . . . . . A . .

100
Jk2:    Y T F G Q G T K L E I K R
F105Vk: C . . . . . . . . . . . .

neu:    C . . . . . . . . . . . .
```

Analysis of the F105 $J_k$ Region Gene

The F105 $J_k$ region is most similar to the germline $J_{k2}$ gene (Table 7, panel A). Codon position 96 is formed by the recombination of $V_k$ and $J_k$ and has two nucleotide changes which results in the non-conservative replacement of Tyr→Cys. A silent T→A nucleotide change also occurs at position 108, otherwise the F105 $J_k$ gene is in $J_k$ germline configuration.

Comparative Analysis of the F105 Rearranged κ Chain With Other Rearranged Humvk325 Related κ Chains Rheumatoid factor antibodies are typically IgMk antibodies and are directed against IgG antibodies. Many IgMk rheumatoid factors use the Humvk325 gene in the germline unmutated configuration [Goñi, et al., *J. Immunol.*, 135:4073–4079 (1985); Silverman, et al., *J. Clin. Invest.*, 82:469–475 (1988)] and several also use the $J_{k2}$ gene in unmutated form [Goñi, et al., supra] as in F105. Table 7 (panel B) compares the amino acid and nucleotide sequence of the rearranged F105 κ chain to the κ chain of the closely related IgMk rheumatoid factor neu. As can be seen, neu is similar to F105 with two identical point mutations in positions 31, Ser→Arg and 96, Tyr→Cys, the latter change occurring as a result of an uncommon V/J joining event.

What is claimed:

1. An isolated DNA segment comprising a nucleotide sequence as defined in the Sequence Listing by SEQ ID NO:1 or SEQ ID NO:3.

2. An isolated DNA sequence containing a promoter operably linked to the DNA sequence of SEQ ID NO:1 and SEQ ID NO:3, wherein expression of the sequence results in expression of an antibody having affinity for a HIV-1 gp120 epitope or neutralizing ability in an in vitro assay for HIV-1.

3. The DNA sequence in claim 2, wherein the resulting antibody is Fab fragment.

4. The DNA sequence of claim 2, wherein the resulting antibody is chain Ab.

5. An isolated DNA segment comprising nucleotides 58–426 of SEQ ID NO:1.

6. An isolated DNA segment comprising nucleotides 58–387 of SEQ ID NO:3.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 426 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 1...426
        ( D ) OTHER INFORMATION:
        ( A ) NAME/KEY: mat_peptide
        ( B ) LOCATION: 58...426
        ( D ) OTHER INFORMATION:

( x i ) SEQUENCE DESCRIPTION: SEQ ID NO:1:

```
ATG GAA CAT CTG TGG TTC TTC CTT CTC CTG GTG GCA GCT CCC AGA TGG      48
Met Glu His Leu Trp Phe Phe Leu Leu Leu Val Ala Ala Pro Arg Trp
-19         -15                 -10                 -5

GTC CTG TCC CAG GTG CAG CTG CAG GAG TCT GGC CCA GGA CTG GTG AAG      96
Val Leu Ser Gln Val Gln Leu Gln Glu Ser Gly Pro Gly Leu Val Lys
             1                   5                   10

CCT TCG GAG ACC CTG TCC CTC ACC TGC ACT GTC TCT GGA GGC TCC ATC     144
Pro Ser Glu Thr Leu Ser Leu Thr Cys Thr Val Ser Gly Gly Ser Ile
        15                  20                  25

AGT AGT CAC TAC TGG AGC TGG ATC CGG CAG TCC CCA GGG AAG GGA CTG     192
Ser Ser His Tyr Trp Ser Trp Ile Arg Gln Ser Pro Gly Lys Gly Leu
30                      35                  40                  45

CAG TGG ATT GGA TAT ATC TAC TAC AGT GGG AGC ACC AAC TAC AGC CCC     240
Gln Trp Ile Gly Tyr Ile Tyr Tyr Ser Gly Ser Thr Asn Tyr Ser Pro
                 50                  55                  60

TCC CTC AAG AGT CGA GTC ACC ATA TCA GTA GAG ACG TCC AAG AAC CAG     288
Ser Leu Lys Ser Arg Val Thr Ile Ser Val Glu Thr Ser Lys Asn Gln
             65                  70                  75

TTC TCC CTG AAG CTG ACC TCT ATG ACC GCT GCT GAC ACG GCC GTG TAT     336
Phe Ser Leu Lys Leu Thr Ser Met Thr Ala Ala Asp Thr Ala Val Tyr
         80                  85                  90

TAT TGT GCA CGA GGC CCC GTC CCA GCT GTC TTC TAC GGT GAC TAC CGA     384
Tyr Cys Ala Arg Gly Pro Val Pro Ala Val Phe Tyr Gly Asp Tyr Arg
     95                  100                 105

CTC GAC CCC TGG GGC CAG GGA ACC CTG GTC ACC GTC TCC TCA             426
Leu Asp Pro Trp Gly Gln Gly Thr Leu Val Thr Val Ser Ser
110                 115                 120
```

( 2 ) INFORMATION FOR SEQ ID NO:2:

( i ) SEQUENCE CHARACTERISTICS:
        ( A ) LENGTH: 142 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:2:

```
Met Glu His Leu Trp Phe Phe Leu Leu Leu Val Ala Ala Pro Arg Trp
-19         -15                 -10                 -5
```

```
Val  Leu  Ser  Gln  Val  Gln  Leu  Gln  Glu  Ser  Gly  Pro  Gly  Leu  Val  Lys
          1              5                        10

Pro  Ser  Glu  Thr  Leu  Ser  Leu  Thr  Cys  Thr  Val  Ser  Gly  Gly  Ser  Ile
     15                  20                       25

Ser  Ser  His  Tyr  Trp  Ser  Trp  Ile  Arg  Gln  Ser  Pro  Gly  Lys  Gly  Leu
30                       35                       40                            45

Gln  Trp  Ile  Gly  Tyr  Ile  Tyr  Tyr  Ser  Gly  Ser  Thr  Asn  Tyr  Ser  Pro
               50                        55                            60

Ser  Leu  Lys  Ser  Arg  Val  Thr  Ile  Ser  Val  Glu  Thr  Ser  Lys  Asn  Gln
               65                        70                  75

Phe  Ser  Leu  Lys  Leu  Thr  Ser  Met  Thr  Ala  Ala  Asp  Thr  Ala  Val  Tyr
          80                      85                       90

Tyr  Cys  Ala  Arg  Gly  Pro  Val  Pro  Ala  Val  Phe  Tyr  Gly  Asp  Tyr  Arg
     95                  100                      105

Leu  Asp  Pro  Trp  Gly  Gln  Gly  Thr  Leu  Val  Thr  Val  Ser  Ser
110                      115                 120
```

( 2 ) INFORMATION FOR SEQ ID NO:3:

( i ) SEQUENCE CHARACTERISTICS:
        ( A ) LENGTH: 387 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 1...387
        ( D ) OTHER INFORMATION:
        ( A ) NAME/KEY: mat_peptide
        ( B ) LOCATION: 58...387
        ( D ) OTHER INFORMATION:

( x i ) SEQUENCE DESCRIPTION: SEQ ID NO:3:

```
ATG  GAA  ACC  CCA  GCG  CAG  CTT  CTC  TTC  CTC  CTG  CTA  CTC  TGG  CTC  CCA    48
Met  Glu  Thr  Pro  Ala  Gln  Leu  Leu  Phe  Leu  Leu  Leu  Leu  Trp  Leu  Pro
-19            -15                      -10                           -5

GAT  ACC  ACC  GGA  GAA  ATT  GTG  TTG  ACG  CAG  TCT  CCA  GGC  ACC  CTG  TCT    96
Asp  Thr  Thr  Gly  Glu  Ile  Val  Leu  Thr  Gln  Ser  Pro  Gly  Thr  Leu  Ser
               1              5                        10

TTG  TCT  GCA  GGG  GAA  AGA  GCC  ACC  CTC  TCC  TGC  AGG  GCC  AGT  CAG  AGT   144
Leu  Ser  Ala  Gly  Glu  Arg  Ala  Thr  Leu  Ser  Cys  Arg  Ala  Ser  Gln  Ser
          15                  20                       25

GTT  AGC  AGC  AGG  TAC  TTA  GCC  TGG  TAC  CAG  CAG  AAA  CCT  GGC  CAG  GCT   192
Val  Ser  Ser  Arg  Tyr  Leu  Ala  Trp  Tyr  Gln  Gln  Lys  Pro  Gly  Gln  Ala
30                       35                       40                           45

CCC  AGG  CTC  CTC  ATC  TAT  GGT  GCA  TCC  AGC  AGG  GCC  ACT  GGC  ATC  CCA   240
Pro  Arg  Leu  Leu  Ile  Tyr  Gly  Ala  Ser  Ser  Arg  Ala  Thr  Gly  Ile  Pro
               50                        55                            60

GAC  AGG  TTC  AGT  GGC  AGT  GGG  TCT  GGG  ACA  GAC  TTC  ACT  CTC  ACC  ATC   288
Asp  Arg  Phe  Ser  Gly  Ser  Gly  Ser  Gly  Thr  Asp  Phe  Thr  Leu  Thr  Ile
               65                        70                            75

AGC  AGA  GTG  GAG  CCT  GAA  GAT  TTT  GCA  GTG  TAT  TAC  TGT  CAG  CAA  TAT   336
Ser  Arg  Val  Glu  Pro  Glu  Asp  Phe  Ala  Val  Tyr  Tyr  Cys  Gln  Gln  Tyr
               80                        85                            90

GAT  AAC  TCC  GTT  TGT  ACT  TTT  GGC  CAG  GGG  ACC  AAG  CTG  GAG  ATC  AAA   384
Asp  Asn  Ser  Val  Cys  Thr  Phe  Gly  Gln  Gly  Thr  Lys  Leu  Glu  Ile  Lys
          95                       100                      105

CGA                                                                              387
Arg
110
```

(2) INFORMATION FOR SEQ ID NO:4:

(i) SEQUENCE CHARACTERISTICS:
　　　　(A) LENGTH: 129 amino acids
　　　　(B) TYPE: amino acid
　　　　(C) STRANDEDNESS: single
　　　　(D) TOPOLOGY: linear (ii) MOLECULE TYPE: protein (v) FRAGMENT TYPE: internal (xi) SEQUENCE DESCRIPTION: SEQ ID NO:4:

```
Met Glu Thr Pro Ala Gln Leu Leu Phe Leu Leu Leu Leu Trp Leu Pro
-19          -15                  -10                      -5

Asp Thr Thr Gly Glu Ile Val Leu Thr Gln Ser Pro Gly Thr Leu Ser
             1                5                  10

Leu Ser Ala Gly Glu Arg Ala Thr Leu Ser Cys Arg Ala Ser Gln Ser
         15              20              25

Val Ser Ser Arg Tyr Leu Ala Trp Tyr Gln Gln Lys Pro Gly Gln Ala
 30              35              40                          45

Pro Arg Leu Leu Ile Tyr Gly Ala Ser Ser Arg Ala Thr Gly Ile Pro
             50              55                          60

Asp Arg Phe Ser Gly Ser Gly Ser Gly Thr Asp Phe Thr Leu Thr Ile
         65              70              75

Ser Arg Val Glu Pro Glu Asp Phe Ala Val Tyr Tyr Cys Gln Gln Tyr
         80              85              90

Asp Asn Ser Val Cys Thr Phe Gly Gln Gly Thr Lys Leu Glu Ile Lys
         95              100             105

Arg
110
```

(2) INFORMATION FOR SEQ ID NO:5:

(i) SEQUENCE CHARACTERISTICS:
　　　　(A) LENGTH: 15 amino acids
　　　　(B) TYPE: amino acid
　　　　(C) STRANDEDNESS: single
　　　　(D) TOPOLOGY: linear (xi) SEQUENCE DESCRIPTION: SEQ ID NO:5:

```
Gly Gly Gly Gly Ser Gly Gly Gly Gly Ser Gly Gly Gly Gly Ser
 1               5                   10                  15
```

(2) INFORMATION FOR SEQ ID NO:6:

(i) SEQUENCE CHARACTERISTICS:
　　　　(A) LENGTH: 10 amino acids
　　　　(B) TYPE: amino acid
　　　　(C) STRANDEDNESS: single
　　　　(D) TOPOLOGY: linear (xi) SEQUENCE DESCRIPTION: SEQ ID NO:6:

```
Asp Arg Val Tyr Ile His Pro Phe His Leu
 1               5                   10
```

(2) INFORMATION FOR SEQ ID NO:7:

(i) SEQUENCE CHARACTERISTICS:
　　　　(A) LENGTH: 35 base pairs
　　　　(B) TYPE: nucleic acid
　　　　(C) STRANDEDNESS: single
　　　　(D) TOPOLOGY: linear (xi) SEQUENCE DESCRIPTION: SEQ ID NO:7:

TTTGCGGCCG CTCAGGTGCA RCTGCTCGAG TCYGG     35

( 2 ) INFORMATION FOR SEQ ID NO:8:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TTAGCGCGCT GAGGTGACCG TTGACCRKGG T     31

( 2 ) INFORMATION FOR SEQ ID NO:9:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TTAGCGCGCA CAAGATTTGG GCTC     24

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TGCTGAGGGA GTAGAGT     17

( 2 ) INFORMATION FOR SEQ ID NO:11:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:11:

TTTGCGGCCG CTGAGCTCSW GMTGACCCAG TCTCCA     36

( 2 ) INFORMATION FOR SEQ ID NO:12:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:12:

CGAGGATCCT TATTAACGCG TGATCTCCAS YTTGGTCCC     39

( 2 ) INFORMATION FOR SEQ ID NO:13:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

CGAGGATCCT TATTAACGCG TTGGTGCAGC CACAGT     36

-continued ( 2 ) INFORMATION FOR SEQ ID NO:14:

( i ) SEQUENCE CHARACTERISTICS:
( A ) LENGTH: 33 base pairs
( B ) TYPE: nucleic acid
( C ) STRANDEDNESS: single
( D ) TOPOLOGY: linear ( x i ) SEQUENCE DESCRIPTION: SEQ ID NO:14:

TGGGGATCCT TATTAACACT CTCCCCTGTT GAA 33

( 2 ) INFORMATION FOR SEQ ID NO:15:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:15:

TTTACCATGG AACATCTGTG GTTC 24

( 2 ) INFORMATION FOR SEQ ID NO:16:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:16:

GGAACCATGG AAACCCCAGC GCAG 24